US009180310B2

(12) United States Patent
Black et al.

(10) Patent No.: US 9,180,310 B2
(45) Date of Patent: *Nov. 10, 2015

(54) BRACHYTHERAPY DEVICES AND RELATED METHODS PROVIDING BIOABSORBABILITY AND/OR ASYMMETRIC IRRADIATION

(71) Applicant: Civatech Oncology, Chapel Hill, NC (US)

(72) Inventors: Robert D. Black, Chapel Hill, NC (US); David Wagner, Raleigh, NC (US); Claudia Black, Chapel Hill, NC (US)

(73) Assignee: Civatech Oncology, Chapel Hill, NC (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/692,197

(22) Filed: Dec. 3, 2012

(65) Prior Publication Data

US 2013/0096360 A1 Apr. 18, 2013

Related U.S. Application Data

(63) Continuation of application No. 12/434,131, filed on May 1, 2009, now Pat. No. 8,323,172.

(60) Provisional application No. 61/049,843, filed on May 2, 2008, provisional application No. 61/096,459, filed on Sep. 12, 2008, provisional application No. 61/150,081, filed on Feb. 5, 2009, provisional application No. 61/166,369, filed on Apr. 3, 2009.

(51) Int. Cl.
*A61M 36/00* (2006.01)
*A61N 5/10* (2006.01)
*G21G 4/08* (2006.01)

(52) U.S. Cl.
CPC ............... *A61N 5/1001* (2013.01); *G21G 4/08* (2013.01); *A61N 2005/1019* (2013.01); *A61N 2005/1025* (2013.01); *Y10T 156/10* (2015.01)

(58) Field of Classification Search
CPC ..................... A61N 5/1001–5/1029; A61N 2005/1019–2005/1025
USPC ..................... 600/1–8; 250/324–326
See application file for complete search history.

(56) References Cited

U.S. PATENT DOCUMENTS 2,475,155 A   7/1949   Rosenblatt ................. 502/333
4,510,924 A   4/1985   Gray
(Continued)

FOREIGN PATENT DOCUMENTS

EP   1008995 A1 *  6/2000   ............... G21G 4/08

OTHER PUBLICATIONS

International Search Report and Written Report (15 pages) corresponding to International Application No. PCT/US09/02702; Mailing Date: Jun. 26, 2009.
(Continued)

*Primary Examiner* — Catherine B Kuhlman
(74) *Attorney, Agent, or Firm* — Myers Bigel Sibley & Sajovec, P.A.

(57) ABSTRACT

Methods of forming a low-dose-rate (LDR) brachytherapy device include depositing a solution comprising a soluble form of a radioactive material on a substrate. A water-insoluble form of the radioactive material is formed on the substrate by chemical precipitation and/or thermal decomposition.

24 Claims, 20 Drawing Sheets

(56) References Cited

U.S. PATENT DOCUMENTS

| | | | |
|---|---|---|---|
| 4,647,679 A | 3/1987 | Panster et al. | |
| 5,137,700 A | 8/1992 | Sloan | 423/32 |
| 5,304,233 A | 4/1994 | Awadalla et al. | 75/741 |
| 5,378,502 A | 1/1995 | Willard et al. | 427/305 |
| 5,558,249 A | 9/1996 | Falcoff | |
| 6,086,942 A * | 7/2000 | Carden et al. | 427/5 |
| 6,143,431 A | 11/2000 | Webster | 428/669 |
| 6,221,440 B1 | 4/2001 | Meyer et al. | 427/537 |
| 6,264,599 B1 | 7/2001 | Slater et al. | |
| 6,293,899 B1 * | 9/2001 | Sioshansi et al. | 600/3 |
| 6,461,433 B1 | 10/2002 | Carden, Jr. et al. | |
| 6,575,887 B1 | 6/2003 | Schrayer | 600/3 |
| 6,575,888 B2 | 6/2003 | Zamora et al. | 600/3 |
| 6,638,205 B1 | 10/2003 | Chan et al. | 600/3 |
| 6,679,824 B1 * | 1/2004 | Reed et al. | 600/7 |
| 7,762,940 B2 | 7/2010 | Henderson et al. | |
| 8,007,427 B2 | 8/2011 | Reed et al. | |
| 8,100,963 B2 | 1/2012 | Roth et al. | |
| 2002/0164812 A1 * | 11/2002 | DeLucas | 436/86 |
| 2003/0084988 A1 | 5/2003 | Terwilliger et al. | 156/244.12 |
| 2004/0126596 A1 | 7/2004 | Zamora et al. | |
| 2007/0020178 A1 | 1/2007 | Weichert et al. | |
| 2007/0021643 A1 | 1/2007 | Lamoureux et al. | |
| 2007/0289865 A1 | 12/2007 | DiFranco et al. | |
| 2008/0058580 A1 | 3/2008 | Black et al. | |
| 2008/0075934 A1 | 3/2008 | Barlow et al. | |
| 2008/0288068 A1 | 11/2008 | Kronowitz | |
| 2009/0131734 A1 * | 5/2009 | Neustadter et al. | 600/8 |
| 2012/0123189 A1 | 5/2012 | Ribbing et al. | |

OTHER PUBLICATIONS

Palladium hydroxide on Chemical Book. 2008. <http://www.chemicalbook.com/ProductChemicalPropertiesCB3267682_EN.htm>.

* cited by examiner

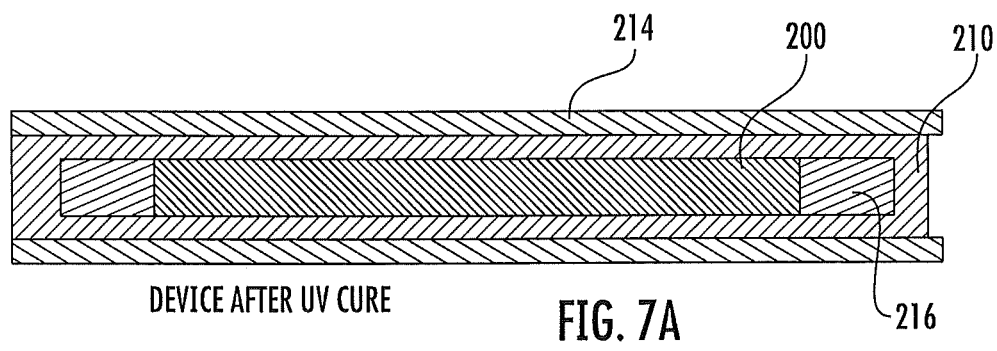
FIG. 7A DEVICE AFTER UV CURE
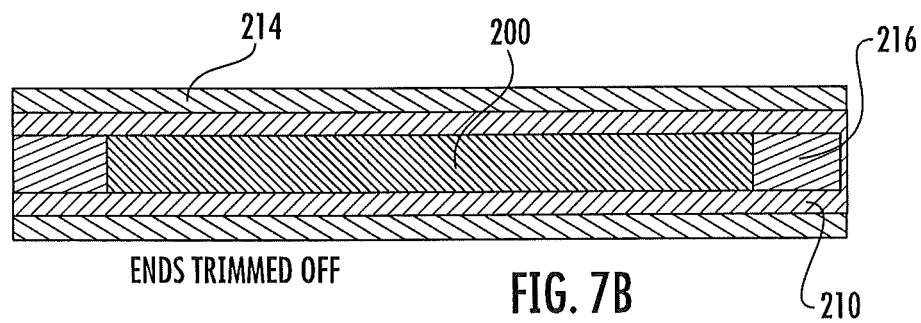
FIG. 7B ENDS TRIMMED OFF
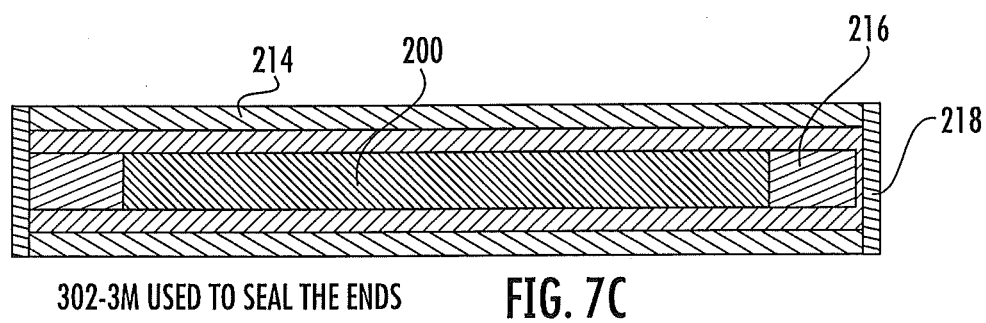
FIG. 7C 302-3M USED TO SEAL THE ENDS

AIR DRY PD COMPOUND

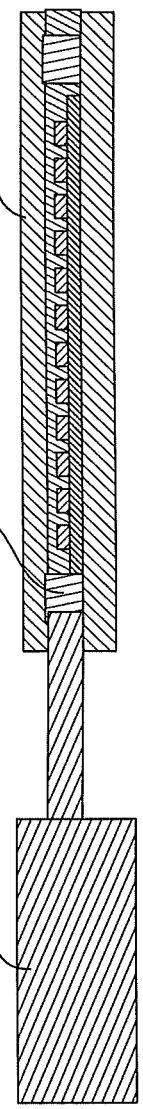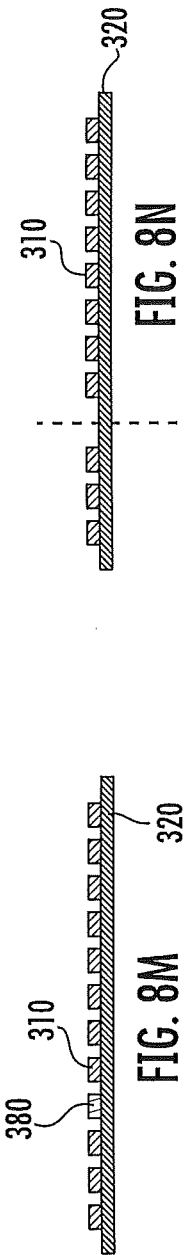

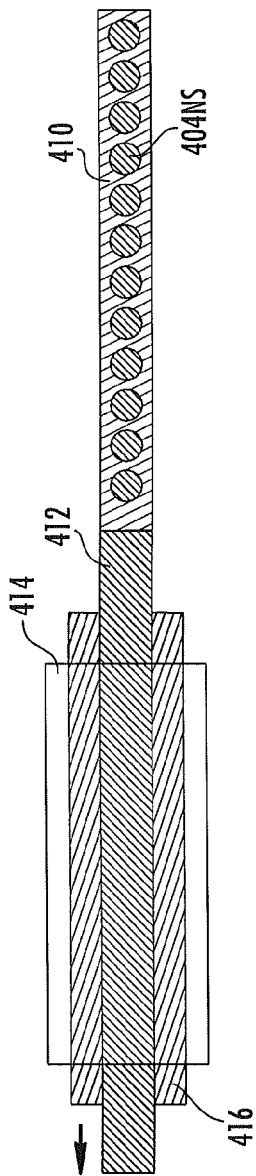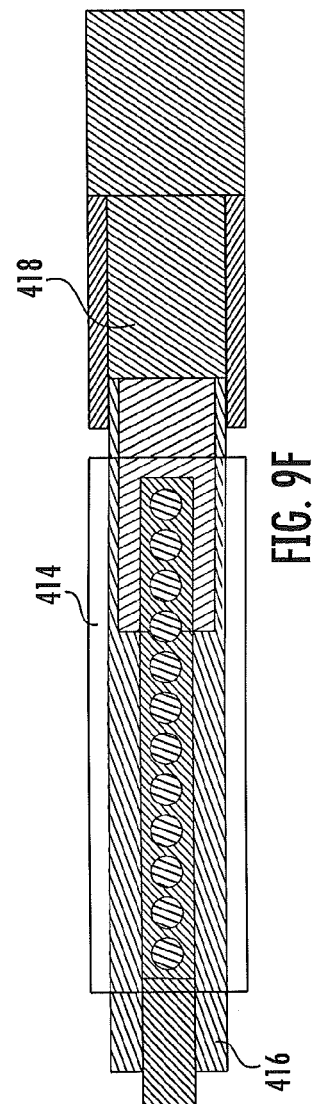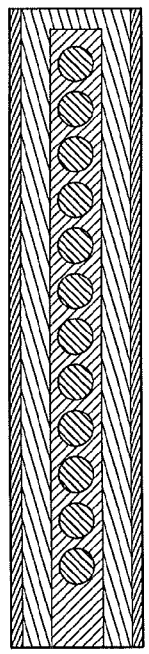
FIG. 9E
FIG. 9F
FIG. 9G

BRACHYTHERAPY DEVICES AND RELATED METHODS PROVIDING BIOABSORBABILITY AND/OR ASYMMETRIC IRRADIATION

RELATED APPLICATIONS

This application is a Continuation of U.S. patent application Ser. No. 12/434,131 filed May 1, 2009 and issued as U.S. Pat. No. 8,323,172 on Dec. 4, 2012 which claims priority to U.S. Provisional Application Ser. Nos. 61/049,843 filed May 2, 2008; 61/096,459 filed Sep. 12, 2008; 61/150,081 filed Feb. 5, 2009; and 61/166,369 filed Apr. 3, 2009, the disclosures of which are hereby incorporated by reference in their entireties.

FIELD OF THE INVENTION

The present invention relates to low-dose rate (LDR) brachytherapy radiation treatment methods, systems and computer program products.

BACKGROUND OF THE INVENTION

Roughly 230,000 new cases of prostate cancer are expected in the U.S. this year. Typically 80-90% of these cases are relatively early stage disease for which various treatment options are available. Primary treatment options involving radiation include external beam radiation therapy, which uses high-energy x-ray beams that intersect the prostate from multiple angles, and brachytherapy, in which a radioactive source is introduced into the prostate itself. Typical brachytherapy techniques use so-called "seeds," which are small (approximately 0.8×4.5 mm) cylinders that contain a radioactive element in a stainless-steel casing. A number of seeds, usually ranging from 80-120 seeds, are placed into the prostate using small gauge needles. The seeds can remain in place permanently while the emitted radiation decays over time. The common radioisotopes used in the seeds are iodine-125, palladium-103 and cesium-131. The goal of the radiation oncologist is to ensure that the total dose received by the cancer cells is sufficient to kill them. Seeds can be placed during an outpatient procedure in a single day and thus present an attractive treatment option for patients versus the many weeks required for external beam radiation therapy. Good candidates for brachytherapy seed therapy are typically patients having a PSA value ≤10, a Gleason score of ≤7 and low-stage disease (T1c or T2a); however, patients with more advanced stage disease may also be treated with brachytherapy. In some cases, patients (e.g., with more advanced disease) may be candidates for brachytherapy plus external beam therapy. The use of seeds has grown rapidly, and long-term survival data for LDR brachytherapy treatment of the prostate is typically good.

In treating prostate cancer with brachytherapy seeds, it may be desirable to create a uniform radiation pattern within the prostate gland or within a region of the prostate gland. Computer code or treatment planning software can be used to select the number of seeds and their relative placement so that the desired radiation dose is achieved. This is a relative complex procedure because each individual seed is essentially a "point source" of radiation, and thus the radiation contributions from all of the seeds must be summed to achieve the total radiation dose. When the seeds are placed, great care is typically taken to ensure that they are arranged in the pattern specified by the treatment planning software. However, some deviation in seed placement may occur due to the divergence of needles as they are inserted. See Nath et al., Med Phys 27, 1058 (2000). A more problematic occurrence is the tendency of seeds to migrate once they exit the insertion needle. See Meigooni et al., Med Phys 31, 3095 (2004). It is not uncommon for seeds to migrate. In some cases, seeds may be caught in an efferent vessel and become embolized in the lung or excreted with urine. Gross movement of the seeds can create non-uniformities in the radiation pattern and thus potentially compromise the efficacy of therapy.

In an attempt to mitigate the post insertion migration of brachytherapy seeds, various products have been developed. For example, the RapidStrand™ device from Oncura (Arlington Heights, Ill., USA) is a hollow suture material that contains conventional seeds in a "linked sausage" arrangement. The suture material subsequently dissolves away leaving the seeds implanted in the patient. However, the seeds are held by the suture for a time that allows for healing and better retention of the seeds. Various so-called "sleeves for seeds" are also available. Another device that is commercially available from IBA (Louvain-la-Neuve, Belgium) under the trade name Radiocoil™ is a coiled structure device that contains rhodium metal that is proton-activated to produce Pd-103. Accordingly, the radioactivity is emitted along the entire length of the device.

Notably, the ability of the radiation oncologist to achieve the highest accuracy in therapy planning is hampered by the discrete nature of the current "seed" radiation sources due to their limited size and anisotropic radiation patterns. The tendency of seeds to move when placed in or near prostatic tissue is a problem that, while not invalidating this excellent form of therapy, creates a non-ideal situation for planning (e.g., requiring revalidation of the placement by CT scan). For example, migration of seeds to the lungs can result in incidental lung doses that are not favorable.

SUMMARY OF EMBODIMENTS OF THE INVENTION

According to some embodiments of the invention, methods of forming a low-dose-rate (LDR) brachytherapy device include depositing a solution comprising a soluble form of a radioactive material on a substrate. The soluble form of the radioactive material is converted to a water-insoluble form of the radioactive material on the substrate. A medical device is formed from the substrate and the water-insoluble form of the radioactive material.

According to some embodiments of the invention, a low-dose-rate (LDR) brachytherapy device includes a substrate having a micropattern thereon. The micropattern includes spaced-apart regions having a water-insoluble form of a radioactive material thereon.

According to some embodiments of the invention, methods of forming a low-dose-rate (LDR) brachytherapy device include depositing a solution comprising a soluble form of a radioactive material on a substrate using a solenoid dispensing system having a controlled pressurized fluid source. The soluble form of the radioactive material is converted to a water-insoluble form of the radioactive material on the substrate. A medical device is formed from the substrate and the water-insoluble form of the radioactive material.

According to some embodiments of the invention, methods of forming a low-dose-rate (LDR) brachytherapy devices include depositing a solution comprising a soluble form of a radioactive material on a bioabsorbable, polymer substrate. The soluble form of the radioactive material is exposed to a plasma treatment for a time sufficient to convert the soluble form of the radioactive material to a water-insoluble form of the radioactive material. A medical device is formed from the substrate and the water-insoluble form of the radioactive material.

According to some embodiments of the invention, methods of forming a low-dose-rate (LDR) brachytherapy device include depositing a radioactive shielding layer on a bioabsorbable, polymer substrate. A solution including a soluble form of a radioactive material is deposited on the radioactive shielding layer opposite the substrate. The soluble form of the radioactive material is exposed to a plasma treatment for a time sufficient to convert the soluble form of the radioactive material to a water-insoluble form of the radioactive material. A medical device is formed from the substrate and the water-insoluble form of the radioactive material. The bioabsorbable, polymer substrate includes a region that is substantially free of the radioactive material. A portion of the region that is substantially free of the radioactive material is cut to customize a shape of the substrate for implantation.

BRIEF DESCRIPTION OF THE DRAWINGS

FIGS. 7A-7C are schematic diagram of a curing step (FIG. 7A), a trimming step (FIG. 7B) and a sealing step (FIG. 7C)

Figure 6A:
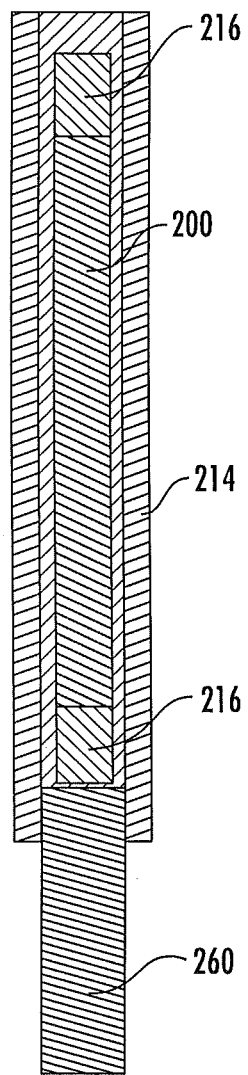
FIG. 6A is a schematic diagram of another brachytherapy device formed from the systems and methods of FIGS. 5A-5D including a radiographic marker.
Figure 8A:
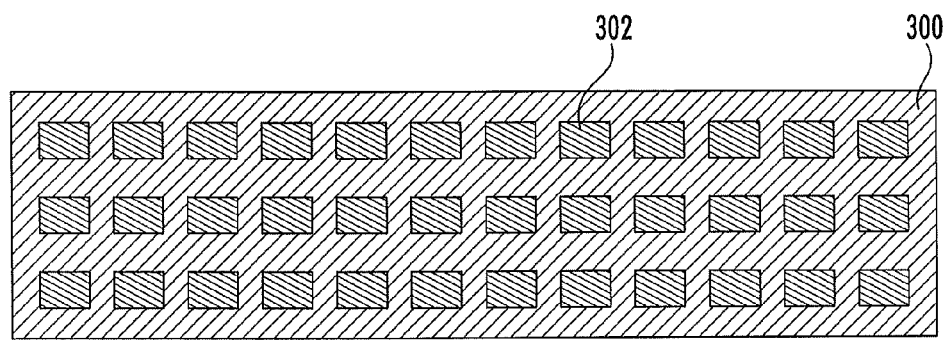
Figure 8B:
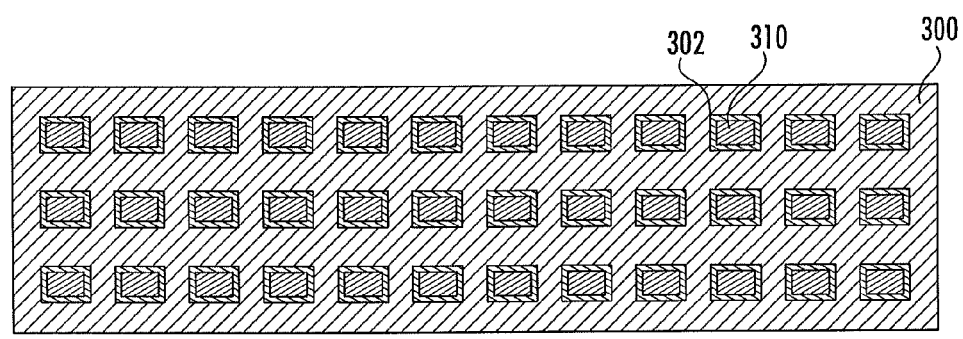
Figure 8C:
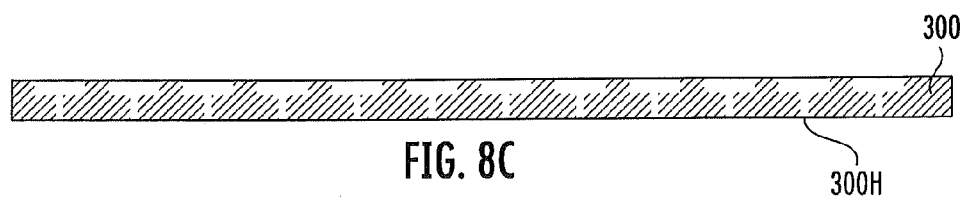
Figure 8D:
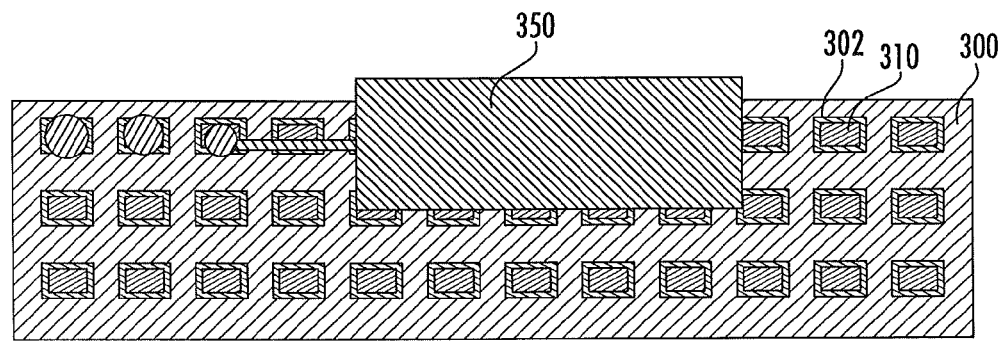
Figure 8E:
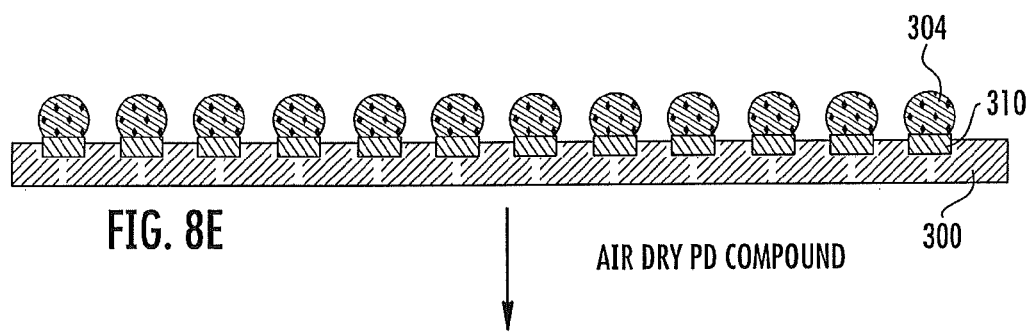
Figure 8F:
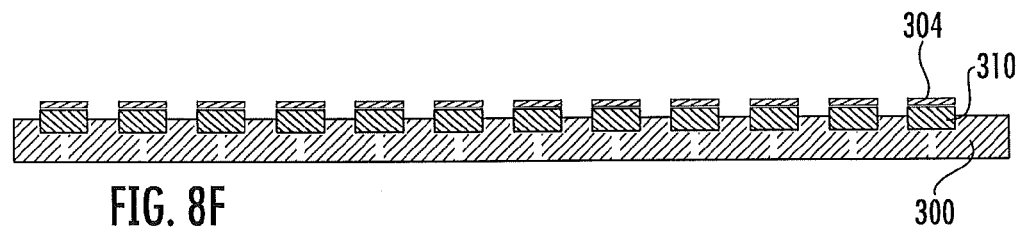
Figure 8G:
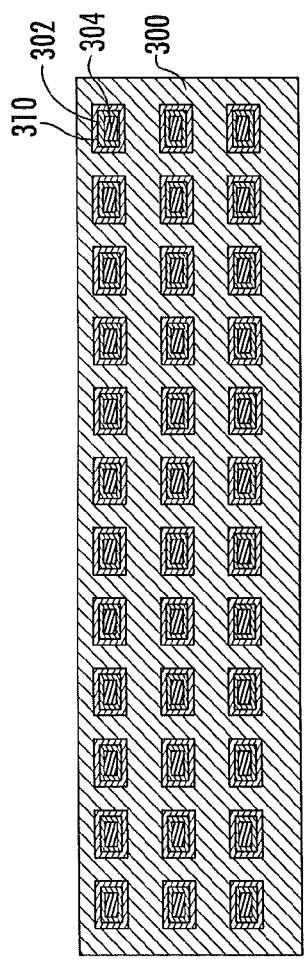
Figure 8H:
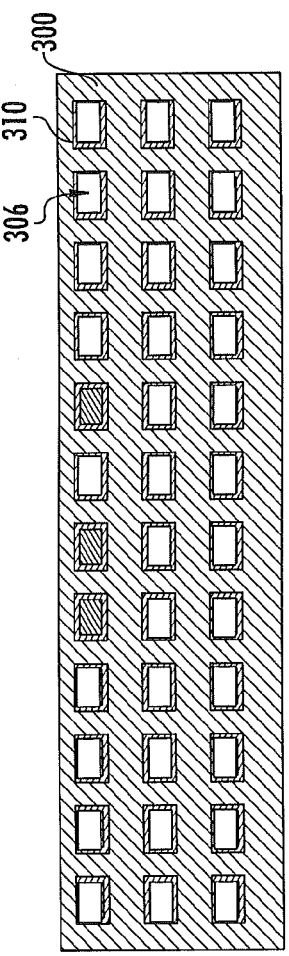
Figure 8I:
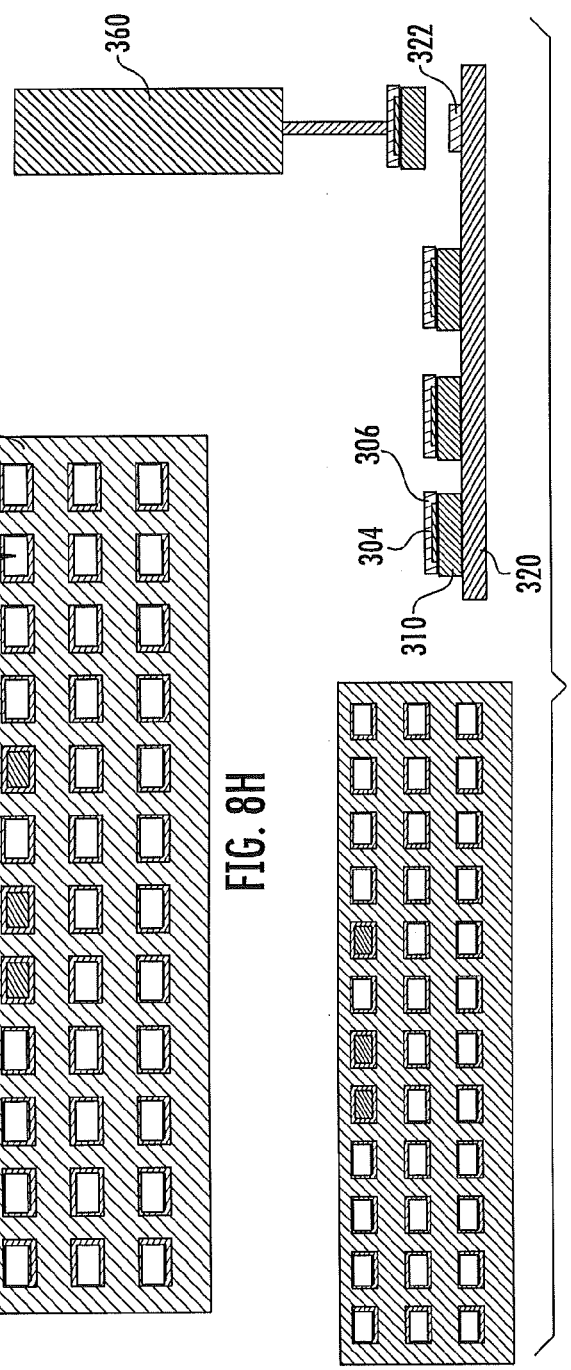
Figure 10:
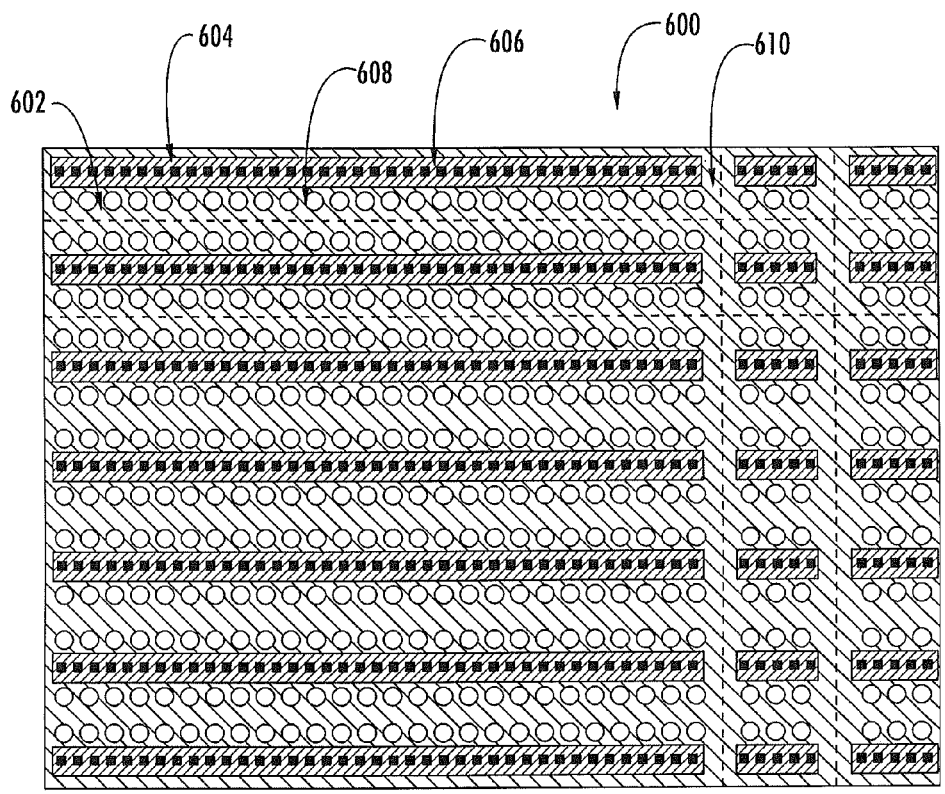
Figure 11:
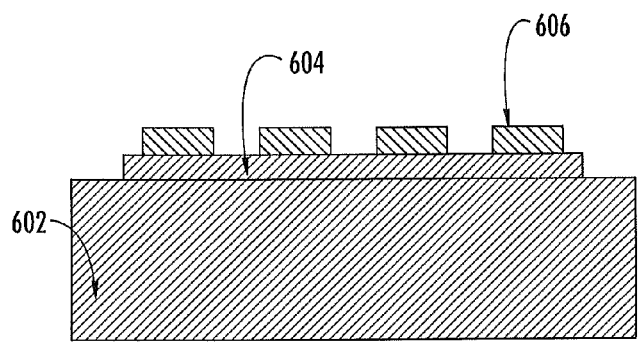

being performed on the device of FIG. 6A according to some embodiments of the present invention;

FIG. 8A is a schematic diagram illustrating a silicon substrate carrier according to some embodiments of the present invention;

FIG. 8B is a schematic diagram of a substrate assembly according to embodiments of the present invention including the silicon substrate carrier of FIG. 8A with silicon substrates therein;

FIG. 8C is a side view of the silicon substrate carrier of FIG. 8A;

FIG. 8D is a schematic diagram of a deposition apparatus that deposits a solution of radioactive material on the silicon substrates of the substrate assembly of FIG. 8B;

FIG. 8E is a side view of the substrate assembly of FIG. 8B with the solution of radioactive material deposited thereon according to some embodiments of the present invention;

FIG. 8F is a side view of the substrate assembly of FIG. 8E after a drying step according to embodiments of the present invention;

FIG. 8G is a top view of the substrate assembly of FIG. 8F after a thermal decomposition step to form a water insoluble radioactive material according to some embodiments of the present invention;

FIG. 8H is a top view of the substrate assembly of FIG. 8G including an additional protective coating on the water insoluble radioactive material according to some embodiments of the present invention;

FIG. 8I is a schematic diagram of a system for adhering the silicon substrates to a polymer carrier core according to some embodiments of the present invention;

FIG. 8J is a schematic diagram illustrating the polymer core of FIG. 8I being inserted into a protective sheath according to some embodiments of the present invention;

FIG. 8K is a schematic diagram illustrating a device for filling the protective sheath of FIG. 8J with epoxy according to some embodiments of the present invention;

FIGS. 8L-8N are schematic diagrams illustrating brachytherapy devices according to some embodiments of the present invention;

FIGS. 9A-9G are schematic diagrams illustrating plasma decomposition techniques and devices according to some embodiments of the present invention;

FIG. 10 is a schematic diagram illustrating a top view of a planar device according to some embodiments of the present invention; and FIG. 11 is a cross sectional view of a portion of the planar device of FIG. 10.

Figure 12A:
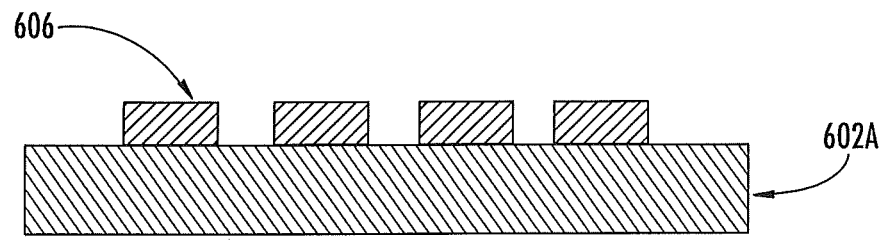
Figure 12B:
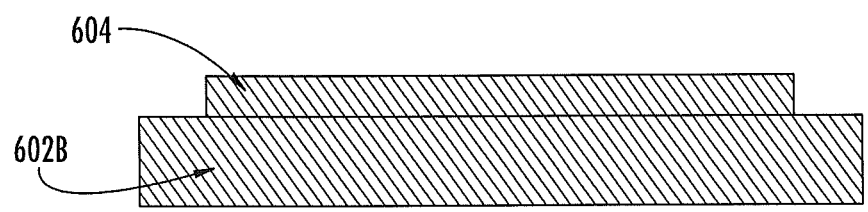
Figure 12C:
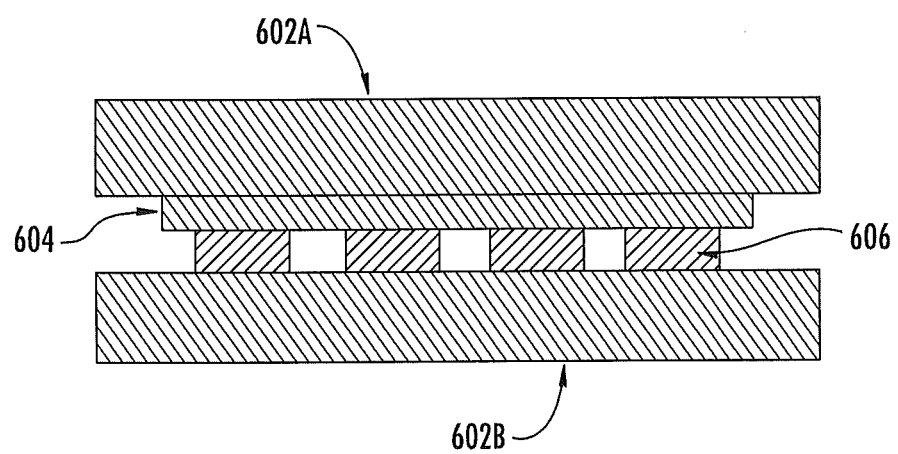

FIGS. 12A-12C are cross sectional views of a portion of a device according to some embodiments of the present invention.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

As used herein, the term "globule" refers to a discrete volume of material. Globules of material can be deposited on a substrate or in a micro-well, for example, using a micro-syringe pump or micro-pipette according to embodiments of the present invention. In some embodiments, the volume of material in globule can be controlled, for example, with an accuracy of better than 10%. Typical sizes of globules are between 5 and 500 nanoliters. In particular embodiments, the globule size is between 30 and 200 nanoliters. In some embodiments, the globules can be spaced apart by about 500-1000 μm.

Radiation treatment devices and fabrication methods are discussed in U.S. Application Ser. Nos. 60/823,814, filed Aug. 29, 2006; 60/847,458, filed Sep. 27, 2006; 60/926,349 filed Apr. 26, 2007; and Ser. No. 11/846,075, filed Aug. 28, 2007, the disclosures of which are hereby incorporated by reference in their entireties.

Figure 1:
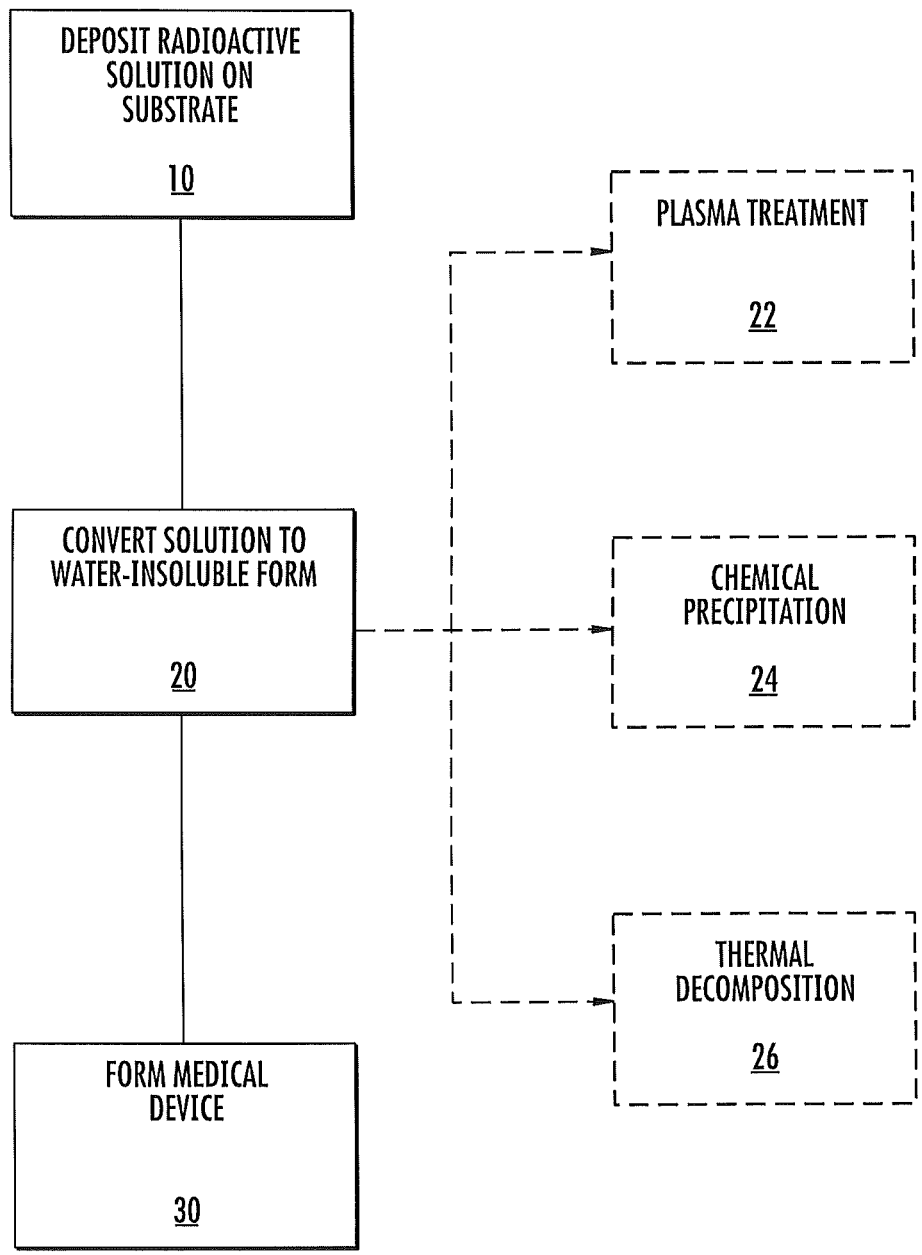
FIG. 1 is a flowchart illustrating operations according to some embodiments of the invention.

As illustrated in FIG. 1, a low-dose-rate (LDR) brachytherapy device can be formed by depositing a solution including a soluble form of a radioactive material on a substrate (Block 10). The soluble form of the radioactive material (e.g., a water-soluble radioactive material) is converted to a water-insoluble form of the radioactive material on the substrate (Block 20). A medical device can be formed from the substrate and the water-insoluble form of the radioactive material (Block 30). Although embodiments according to the invention are discussed herein with respect to converting a water-soluble form of a radioactive material into a water-insoluble form, it should be understood that the solution deposited on the substrate at Block 10 may include solvents in addition to or in place of water, such as HCl. Thus, the soluble form of the radioactive material may be water-soluble or soluble in a solvent other than water without departing from the scope of the invention.

The water-insoluble form of the radioactive material can be formed by various techniques, including plasma decomposition (FIG. 1; Block 22), chemical precipitation (FIG. 1; Block 24), thermal decomposition (FIG. 1; Block 26) and/or combinations thereof.

Figure 2A:
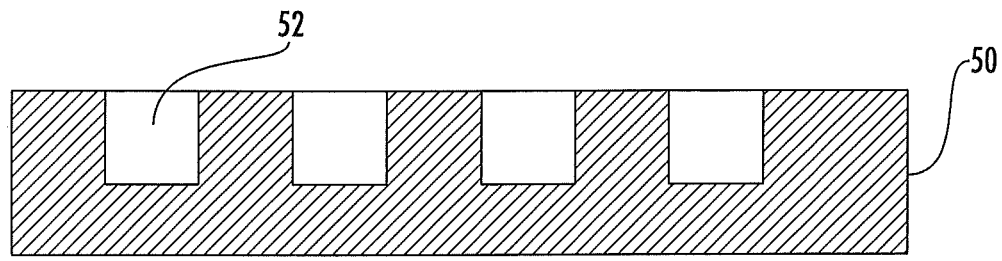
FIGS. 2A-2D are cross-sectional views of devices having a substrate with a well pattern and a radioactive material therein according to some embodiments of the invention.
Figure 2B:
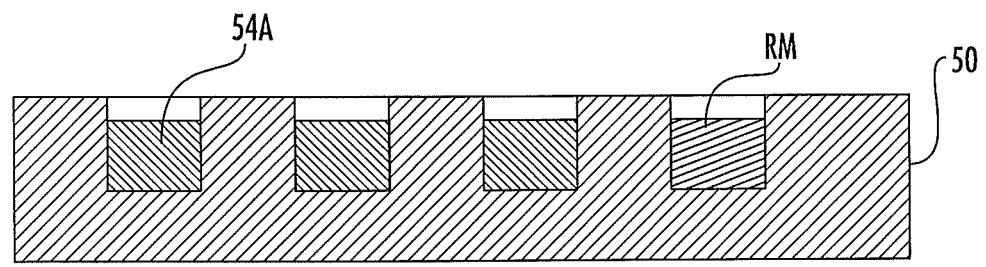
Figure 2C:
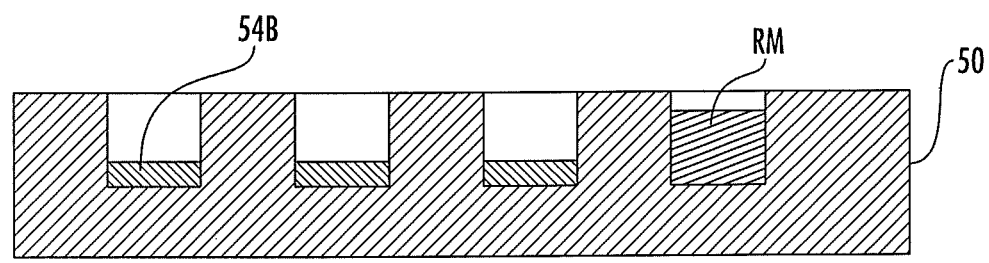
Figure 2D:
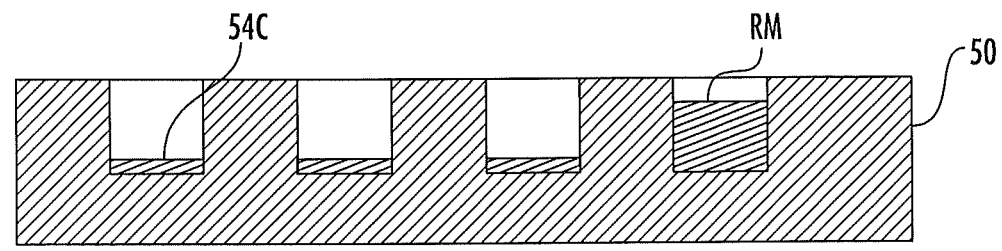

For example, as shown in FIGS. 2A-2D, a substrate 50 is provided with microwells 52 therein. The substrate 50 can be a polymer substrate such as a nylon substrate. The selection of the polymer will be within the skill of one in the art. A volume of radioactive salt solution 54A is deposited in the microwell 52 as shown in FIG. 2B. The radioactive salt solution 54A can be deposited using a microsyringe, pipette or a solenoid dispensing system as described herein. The radioactive salt solution can be [Pd(NH$_3$)$_4$]Cl$_2$ dissolved in ammonium hydroxide (NH$_4$OH) and/or PdCl$_2$ dissolved in HCl; however, other suitable solutions can be used. The salt solution 54A is optionally dried to provide a dried salt 54B as shown in FIG. 2C. The salt 54B is then decomposed into a water-insoluble radioactive material 54C as shown in FIG. 2D, for example, by chemical, thermal or plasma decomposition as described herein. For example, palladium salt, such as [Pd(NH$_3$)$_4$]Cl$_2$, can be thermally decomposed at temperatures of between about 220-300° C. and/or plasma decomposition can be performed, e.g., using a 50-150 mTorr (or greater) oxygen plasma for at least about 15-30 minutes at a power setting of 200 watts. PdCl$_2$ can be decomposed at about 675° C., and [Pd(NH$_3$)$_4$]Cl$_2$ can be decomposed at about 290° C. In some embodiments, a radio marker RM can be included in one of the wells 52 (e.g., a gold marker) to increase visibility of the device during medical imaging.

Figure 2E:
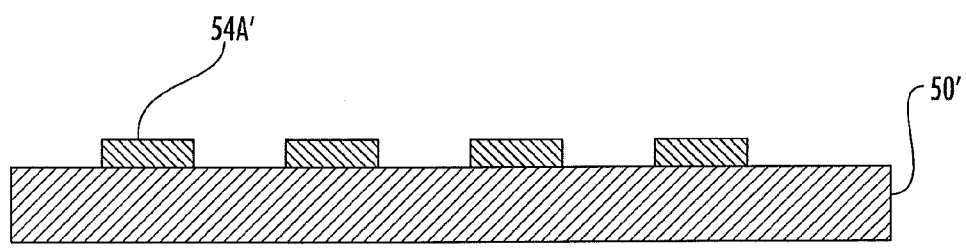
FIGS. 2E-2G are cross-sectional views of devices having a generally smooth substrate and a radioactive material thereon according to some embodiments of the invention.
Figure 2F:
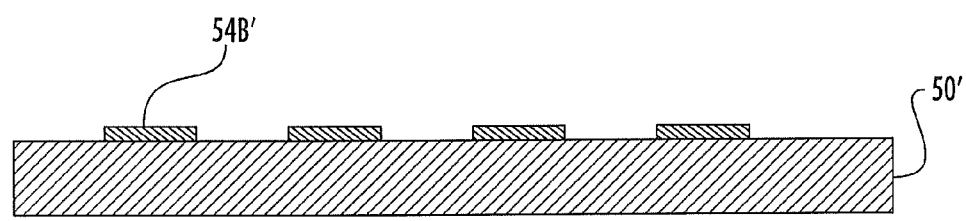
Figure 2G:
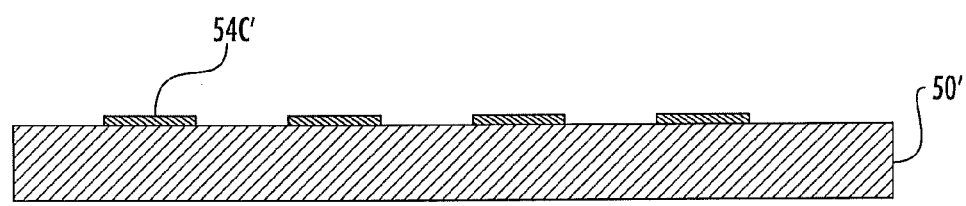

Although a well pattern on the substrate 50 is illustrated in FIGS. 2A-2D, any suitable substrate can be used. As shown in FIGS. 2E-2G, in some embodiments, the substrate 50' can have a generally planar or smooth surface. The radioactive solution 54A' can be deposited in a spaced-apart pattern on the substrate 50'. The radioactive solution 54A' can be evaporated as shown in FIG. 2F to form a solution 54B'. The solution 54B' is then decomposed or converted into a water-insoluble radioactive material 54C'.

Figure 2H:
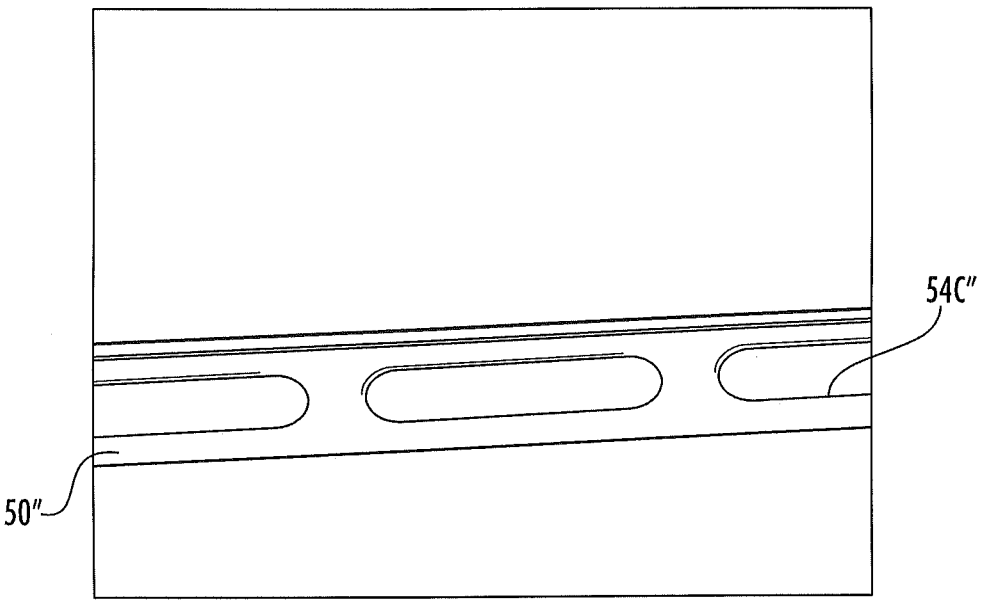
FIG. 2H is a digital image of a micropatterned elongated substrate according to some embodiments of the present invention.
Figure 2I:
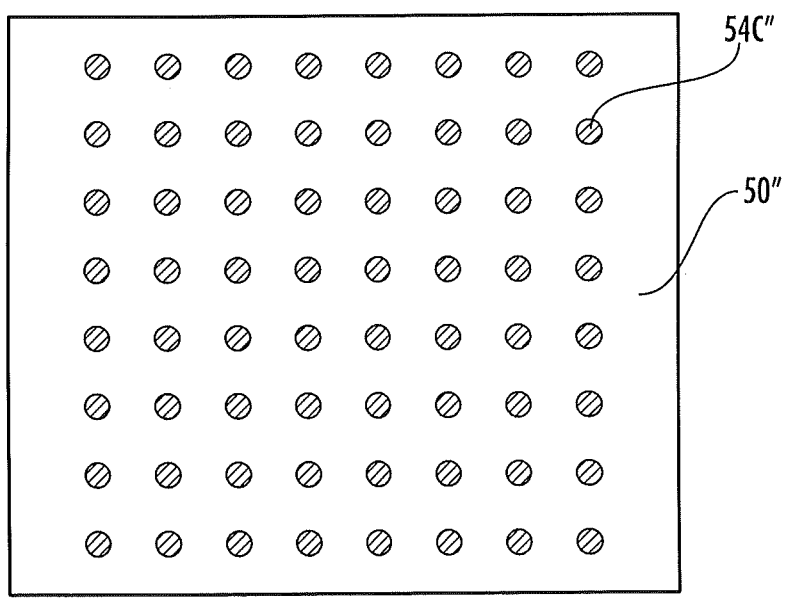
FIG. 2I is a top view of a two dimensional, planar device according to some embodiments of the present invention.

The substrate 50, 50' and water-insoluble radioactive material 54C, 54C' of FIGS. 2D and 2G can be coated with a suitable biocompatible coating and formed into a medical device, such as a elongated strand or a generally planar brachytherapy device. For example, an elongated strand substrate 50" with a water-insoluble radioactive material 54C" is shown in FIG. 2H. An elongated substrate 50''' with a water-insoluble radioactive material 54C''' in a two dimensional, spaced-apart pattern is shown in FIG. 2I. It should be understood that elongated (linear) strand substrates and planar substrates can be formed with microwells, such as the wells 52 shown in FIGS. 2A-2D, or on a substrate without a microwell pattern, such as a generally smooth surface as shown in FIGS. 2E-2G.

In some embodiments shown in FIGS. 2A-2D, the solution 54A includes $Pd(NH_3)_4Cl_2$, and dilute HCl (hydrochloric acid) is added to the solution 54A prior to the drying step shown in FIG. 2C. Without wishing to be bound by any one theory, when HCl is added to $Pd(NH_3)_4Cl_2$, a $Pd(NH_3)_2Cl_2$ precipitate is formed. A precipitate can be at least partially formed before the evaporation of the solution 54A, which can reduce uneven deposits of the salt after evaporation (e.g., ring patterns), which can affect the decomposition time in the plasma.

Accordingly, adding dilute HCl to the solution 54A can lead to a more uniform dispersion of particles in the dried salt 54B of FIG. 2C, and HCl can also facilitate complete and rapid decomposition, for example, in a subsequent plasma process. In some embodiments, a deposition device, such as an isolated solenoid dispensing system (such as is available from Innovadyne Technologies, Inc., Santa Rosa, Calif. (U.S.A.)) can be used to deposit a volume of $Pd(NH_3)_4Cl_2$ (e.g., 75 ml) into a well 52 followed by another volume (e.g., 25 nl) of dilute HCl. Adding HCl may produce ammonium chloride ($NH_4Cl$); however, $NH_4Cl$ may be decomposed in the subsequent oxygen plasma and may be removed at the end of the processing.

In some embodiments, the substrate 50 is treated with a plasma (such as oxygen plasma) before the radioactive salt solution 54A is deposited in FIG. 2B. In particular embodiments, the plasma treatment may be performed at a pressure of 75-100 mTorr with a power setting of 230 Watts for 2-5 minutes, such as for about 3 minutes. The amount of plasma pre-treatment can be modified to provide sufficient dispersal of the salt residue within the well 52. Without wishing to be bound by any one theory, it is believed that plasma surface treatment can function to create surface roughening and/or "activation" of surface binding sites that favor relatively even dispersal of the salt residue within the well 52 and reduce clumping. If the plasma process is performed for an excessive amount of time, the solution 54A can spread out of the well and thus reduce containment of the palladium metal within the well 52. It should be understood that the plasma pre-treatment process described above can be performed on any suitable polymer substrate.

Although the techniques for converting the solution 54A into the water-insoluble radioactive material 54C is described above with respect to FIGS. 2A-2D, it should be understood that such techniques can be applied to substrates having other configurations, including the substrate of FIGS. 2F-2I.

It should be understood that a radiation detector can be used to test the radiation on the resulting medical device. Devices according to embodiments of the present invention can be used as low dose radiation brachytherapy devices, such as for prostate cancer, lung cancer and/or breast cancer.

In some embodiments, the water-insoluble form of the radioactive material can be formed by exposing the substrate and the water-soluble form of the radioactive material to plasma to thereby decompose the water-soluble form of the radioactive material to a water-insoluble form. In some embodiments, a hydrogen or oxygen plasma is used, typically at atmospheric pressure or in a partial vacuum. Although any suitable substrate material and/or radioactive material can be used, in particular embodiments, a polymer substrate can be used. The water-soluble form of the radioactive material can be a salt of Pd-103, such as tetraaminopalladium chloride. For example, a 50-75 mTorr oxygen plasma was found to decompose a dried residue of tetraaminopalladium chloride in about 30 minutes at a power setting of 200 watts. Elemental analysis of the post-plasma residue confirmed that only Pd metal remained. Plasma decomposition of non-radioactive water-soluble materials are described, for example, in Korovchenko et al., Catalysis Today 102-103 (2005) 133-141, and in U.S. Pat. No. 6,383,575, the disclosures of which are hereby incorporated by reference in their entireties.

A brachytherapy medical device can be formed, for example, by enclosing the substrate and the water-insoluble form of the radioactive material (e.g., the substrates 50, 50', 50" and 50''') with a biocompatible material. In some embodiments, polymer microwells as described herein can be used to receive drops or globules of the water-soluble radioactive material in a spaced apart pattern. Alternatively, the water-soluble radioactive material can be deposited on a substantially planar substrate, e.g., in a spaced apart pattern. After the water-soluble form of the radioactive material is converted to a water-insoluble form, a polymer sheet can be adhered on the substrate to laminate the substrate and the water-insoluble form of the radioactive material. Elongated portions of the substrate can be cut or separated to thereby form a brachytherapy strand or a planar sheet. The brachytherapy strand can be positioned in a biocompatible tube, and the tube can be filled, e.g., with a curable thermoplastic resin such as epoxy, and cured such that the radioactive material is sealed. Shielding materials can be added, for example, on one side of the device, to provide reduced irradiation on a side of the device as desired using a radiation treatment plan.

Exemplary dimensions of micropatterned wells are about 250 μm wide, around 300 μm deep, and about 650-1500 μm long. Other dimensions may be about 100-400 μm wide, around 100-500 μm deep and about 650-1500 μm long. The spacing between the wells can range between about 100 μm to about 250 μm.

In some embodiments, the radioactive material is selectively deposited (e.g., in globules) on the micropattern to provide non-uniform and/or discontinuous radiation pattern. Examples of suitable substrates include a suture, such as a monofilament suture, or other biodegradable or non-biodegradable material that is biocompatible and can be implanted in a patient, such as a silicon, glass or metal fiber. Biodegradable materials include, but are not limited to, polydioxanone, polylactide, polyglycolide, polycaprolactone, and copolymers thereof. Copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Non-biodegradable materials include nylon, polyethylene terephthalate (polyester), polypropylene, expanded polytetrafluoroethylene (ePTFE), glass and metal (e.g. stainless steel), metal alloys, or the like.

In some embodiments, a low-dose radiation (LDR) brachytherapy device is formed by determining a radiation profile for the device based on a patient radiation treatment plan and depositing a radioactive material on the device in a pattern. The radioactive material can include a molecularly dispersed radioisotope. The pattern can include a plurality of spaced-apart, discrete globules, each globule having a respective volume of the radioactive material.

In particular embodiments, a water soluble radioactive material in a solution is deposited on the substrate, and a water-insoluble form or precipitate of the radioactive material is formed on the substrate by chemical precipitation, plasma treatment and/or thermal decomposition. A solution having a water soluble radioactive material dispersed therein can provide a known amount of radiation because the radioactive material can be evenly dispersed in the solution. Therefore, the amount of radiation deposited on the substrate is proportional to the volume of solution deposited. However, a water soluble radioactive material can present containment and/or leakage problems in medical devices because water soluble materials may leach into the body. According to embodiments of the present invention, the water soluble form of the radioactive material is converted to a water-insoluble precipitate or form, e.g., by chemical precipitation, by plasma treatment or by thermal decomposition.

For example, the water-insoluble form of the radioactive material can be formed by thermal decomposition by heating the substrate, for example, at a temperature above a decomposition temperature of the radioactive material. The radioactive solution can include a palladium salt, and the decomposition temperature of the palladium salt can be about 290° C. for $Pd(NH_3)_2Cl_2$. Certain polymer materials, such as silicon, can withstand temperatures around 290° C. or higher, and therefore, can be used to form the substrate. However, the decomposition temperature of $PdCl_2$ is 675° C. In particular embodiments, a plurality of spaced-apart, hydrophilic regions are formed on a hydrophobic region of the substrate, and the solution is deposited on some of the plurality of spaced-apart, hydrophillic regions. Accordingly, the solution can adhere to the hydrophillic regions. In particular embodiments, the substrate is silicon and the plurality of spaced-apart, hydrophilic regions are silicon dioxide. In certain embodiments, a silicon substrate (optionally including a hydrophilic region of silicon dioxide) can be fixed or adhered to a polymer core.

In other embodiments, forming a water-insoluble precipitate or form of the radioactive material includes chemically forming the precipitate using a precipitation solution. For example, the solution can be deposited in a plurality of spaced-apart wells on the substrate. A suitable precipitation solution can be added to the wells to chemically precipitate the radioactive material. The remaining solution can be removed, for example, by drying.

In some embodiments, the radioactive material is palladium-103 (Pd-103). For example, a solution including a water-soluble form of Pd-103 can include $[Pd(NH_3)_4]Cl_2$ and/or $PdCl_2$. In particular embodiments, the solution can be $[Pd(NH_3)_4]Cl_2$ dissolved in ammonium hydroxide ($NH_4OH$) and/or $PdCl_2$ dissolved in HCl. For example, the water-insoluble form can be formed by adding sodium borohydride ($NaBH_4$) to the $[Pd(NH_3)_4]Cl_2$ and/or $PdCl_2$ to chemically precipitate water insoluble Pd-103. The molar concentration of $NaBH_4$ can be at least twice the molar concentration of palladium ion. The sodium borohydride ($NaBH_4$) can be buffered in NaOH, e.g., to stabilize the sodium borohydride and/or substantially prevent the sodium borohydride from breaking down in the water solution. It is noted that sodium borohydride generally decomposes in pure water and produces hydrogen gas and sodium borate ($NaBO_2$); however, sodium hydroxide can lower the pH of the solution and reduce this decomposition of the sodium borohidride. In particular embodiments, a 20% (by weight) solution of NaOH and a 7.6% solution (by weight) of sodium borohydride can be used. In certain embodiments, a solution of about 2.4% of sodium borohydride and as little as 1% NaOH can be used for a 56 mg/ml $PdCl_2$ solution. An excess of moles of sodium borohydride versus moles of palladium can be desirable so that substantially all of the palladium is precipitated (a molar ratio of at least 2, as noted above, may be sufficient). Specifically, the ratios chosen for the precipitation solution can be selected for concentrations of palladium around 56 mg/ml or more of $PdCl_2$ (palladium chloride, which can be used as a precursor for either acid or base forms of the solution). In some embodiments, the molar concentration of NaOH is as low as feasible so as to provide buffering against rapid hydrolysis of sodium borohydride. For example, the molar concentration of NaOH can be about 0.25.

In certain embodiments, the substrate includes aluminum and the solution can be deposited on the aluminum substrate to chemically precipitate water insoluble Pd-103. In other embodiments, aluminum is added to the solution to chemically precipitate water insoluble Pd-103.

In some embodiments, the radioactive material comprises I-125 and can be provided as NaI (sodium iodide). The water soluble solution can include NaI dissolved in NaOH. $AgNO_3$ can be added to the NaI to chemically precipitate AgI.

Substrates according to embodiments of the present invention can be coated with a biocompatible coating, such as a polyurethane sleeve, for example, having a thickness greater than 150 micrometers.

In some embodiments, a plurality of hydrophillic regions are spaced apart by hydrophobic regions, and the water insoluble precipitate of the radioactive material is on at least some of the plurality of hydrophillic regions. For example, the substrate can be formed of silicon and the plurality of spaced-apart, hydrophilic regions can be silicon dioxide, which are optionally affixed to a polymer core.

In particular embodiments, the radioactive material can include two radioisotopes having respective decay profiles. Accordingly, the spatial pattern and the at least two different decay profiles can provide a spatiotemporal radiation profile that can be fabricated to implement a radiation therapy plan for an individual patient. For example, ratio of two or more isotopes can be modified to achieve a time-varying radiation profile and can be used to increase the radiobiological effectiveness of the LDR therapy. In some embodiments, different isotopes of the same element can be used.

In some embodiments, the output of conventional radiation therapy planning software or other suitable radiation therapy plans can be used to determine the spatial and/or temporal radiation profile for a device. An example of radiation therapy planning software is VariSeed™ from Varian, Inc. (Palo Alto, Calif.). The device can be fabricated using calculated amounts of radioactive material, such as a radioactive material, that can be dispersed in a spatial pattern along a length of an elongated LDR device and/or using a mixture of two or more isotopes to achieve an appropriate temporal profile.

The radiation therapy plan and spatial and/or temporal radiation profile of the device can take into account the effects of post-implantation edema, e.g., by adding extra length to the device and/or increasing the radioactivity of the proximal and distal ends of the device that can be implanted at an outer boundary of the tumor or organ. In particular embodiments, the device can include a filament that can extend outside the patient after implantation. The filament can have sufficient tensile strength to allow a physician to pull the brachytherapy device in the proximal direction to readjust the position of the device after placement. Once final positioning is achieved, the filament can be severed close to the skin surface.

In particular embodiments, computer program products can be used to determine a pattern of radioactive portions and non-radioactive portions of a device and/or mixture(s) of radioisotopes to create a spatial and/or temporal radiation profile when implanted in the patient and/or to control the fabrication of the brachytherapy device.

Brachytherapy devices can be provided that include a polymeric material having a chemically distributed therapeutic isotope throughout.

In specific embodiments, processing techniques can be used to form radioactive materials, e.g., to form polymeric fibers of the requisite dimensions for use in LDR (low-dose-rate) brachytherapy. Exemplary materials are discussed herein. However, any suitable radioactive material, including radioactive materials or materials that can become radioactive through irradiation, can be used.

Figure 3:
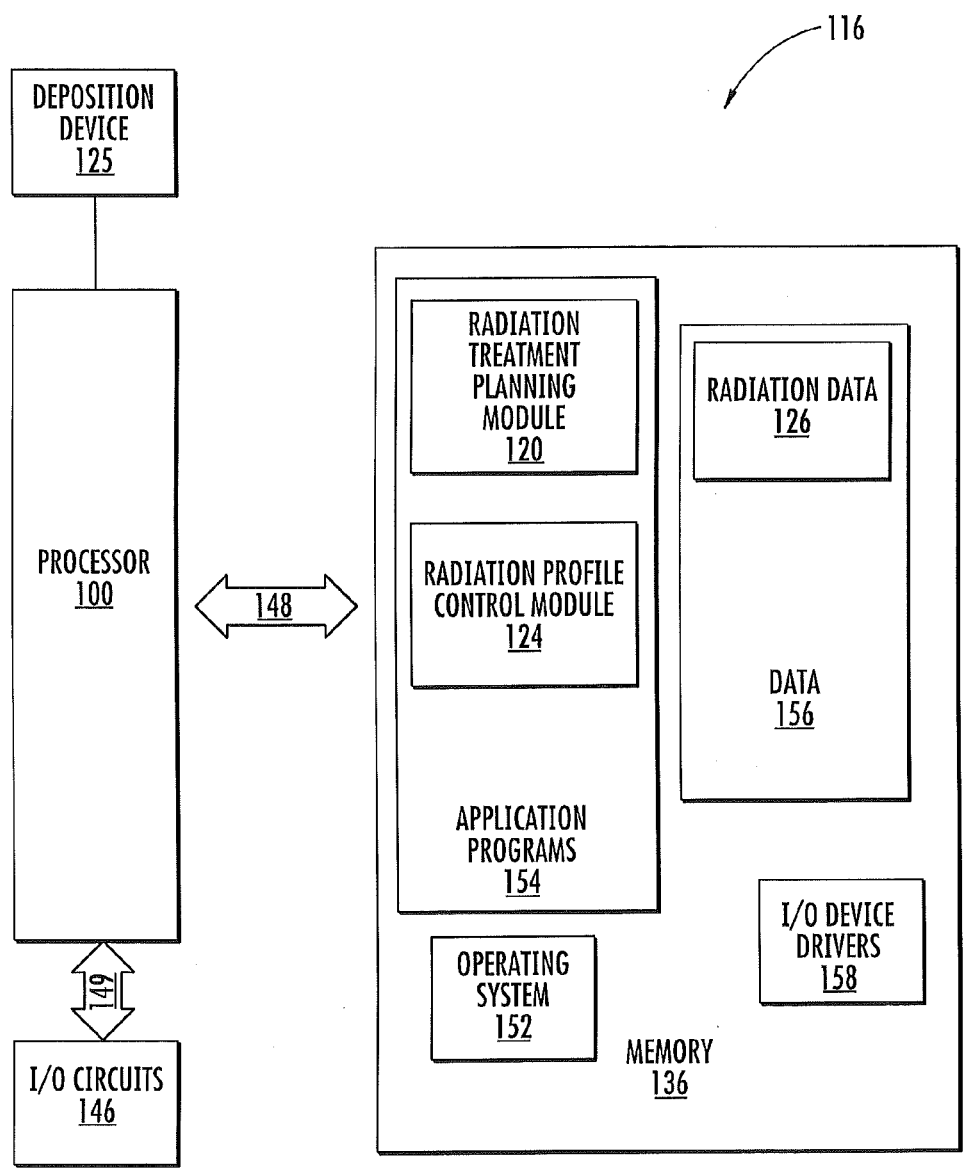
FIG. 3 is a block diagram illustrating methods, systems and computer program products according to some embodiments of the present invention.

FIG. 3 illustrates an exemplary data processing system that can be included in devices operating in accordance with some embodiments of the present invention. As illustrated in FIG. 3, a data processing system 116, which can be used to carry out or direct operations includes a processor 100, a memory 136 and input/output circuits 146. The data processing system can be incorporated in a portable communication device and/or other components of a network, such as a server. The processor 100 communicates with the memory 136 via an address/data bus 148 and communicates with the input/output circuits 146 via an address/data bus 149. The input/output circuits 146 can be used to transfer information between the memory (memory and/or storage media) 136 and another component, such as a deposition controller, beam controller or irradiation device for selectively patterning a brachytherapy device with radiation or radioactive material. These components can be conventional components such as those used in many conventional data processing systems, which can be configured to operate as described herein.

In particular, the processor 100 can be commercially available or custom microprocessor, microcontroller, digital signal processor or the like. The memory 136 can include any memory devices and/or storage media containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 can be a content addressable memory (CAM).

As further illustrated in FIG. 3, the memory (and/or storage media) 136 can include several categories of software and data used in the data processing system: an operating system 152; application programs 154; input/output device circuits 146; and data 156. As will be appreciated by those of skill in the art, the operating system 152 can be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device circuits 146 typically include software routines accessed through the operating system 152 by the application program 154 to communicate with various devices. The application programs 154 are illustrative of the programs that implement the various features of the circuits and modules according to some embodiments of the present invention. Finally, the data 156 represents the static and dynamic data used by the application programs 154, the operating system 152 the input/output device circuits 146 and other software programs that can reside in the memory 136.

The data processing system 116 can include several modules, including a radiation treatment planning module 120, a radiation profile control module 124, and the like. The modules can be configured as a single module or additional modules otherwise configured to implement the operations described herein for planning a radiation treatment plan, determining a spatial and/or temporal radiation profile for a device and/or controlling the deposition of radioactive material or other materials described herein (such as a precipitation solution) on a device to form a desired radiation pattern. The data 156 can include radiation data 126, for example, that can be used by the radiation treatment planning module 120 and/or radiation profile control module to design and/or fabricate a brachytherapy device. The radiation profile control module 124 can be configured to control a deposition device 125.

While the present invention is illustrated with reference to the radiation treatment planning module 120, the radiation profile control module 124 and the radiation data 126 in FIG. 3, as will be appreciated by those of skill in the art, other configurations fall within the scope of the present invention. For example, rather than being an application program 154, these circuits and modules can also be incorporated into the operating system 152 or other such logical division of the data processing system. Furthermore, while the radiation treatment planning module 120 and the radiation profile control module 124 in FIG. 3 is illustrated in a single data processing system, as will be appreciated by those of skill in the art, such functionality can be distributed across one or more data processing systems. Thus, the present invention should not be construed as limited to the configurations illustrated in FIG. 3, but can be provided by other arrangements and/or divisions of functions between data processing systems. For example, although FIG. 3 is illustrated as having various circuits and modules, one or more of these circuits or modules can be combined, or separated further, without departing from the scope of the present invention.

Figure 4A:
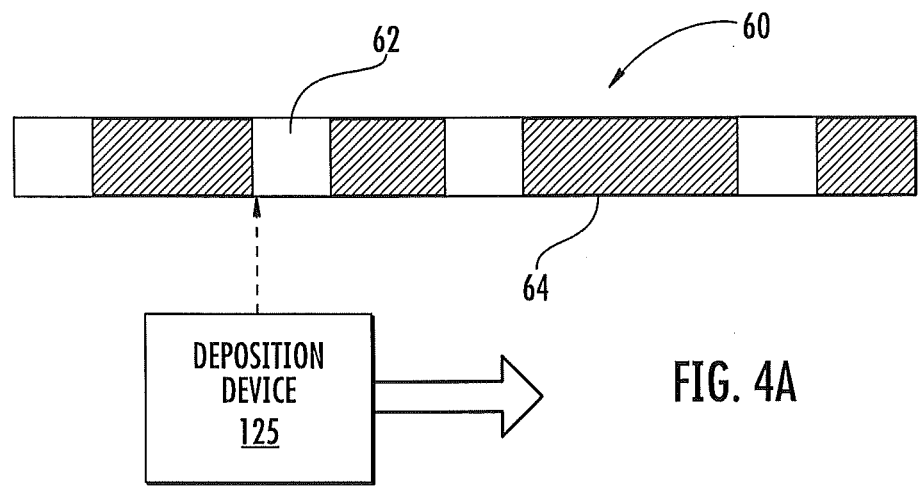
FIG. 4A is a schematic diagram illustrating a deposition configuration for selectively depositing a material on a brachytherapy device according to some embodiments of the present invention.

As shown in FIG. 4A, a deposition device 125 is controlled by a deposition controller (e.g., the radiation profile control module 124 via the I/O circuits 146 of FIG. 3) to form the radioactive portions 62 of the device 60. In particular, the radioactive material can be deposited in a plurality of spaced-apart, discrete globules. Each globule of radioactive material can include a particular volume of the material so that the pattern of radioactive material provide a desired radioactive profile. The globules can have relatively precisely deposited volumes between 5 and 500 nanoliters or between 10 and 200 nanoliters. Two or more radioisotopes can be used to provide a desired decay profile, which can vary along a length of the device. In some embodiments, the volume of the radioactive material can be calculated by the radiation treatment planning module 120 and/or radiation profile control module 124 of FIG. 3. Without wishing to be bound by theory, the amount of radioactive material is generally directly related to the amount of radiation emitted. For example, twice the amount of a radioactive material will generally result in twice the amount of radiation being emitted. Accordingly, in some embodiments, precision deposition can be used to deposit desired amounts of radioactive material to achieve a particular radiation profile.

The deposition device 125 can be a micropipette, a microsyringe pump, or other suitable extrusion and/or deposition device, such as an Ultramicrosyringe II by World Precision Instruments, LTD, Stevenage, Hertfordshire, England. The deposition device 100 can deposit a volume of material with an accuracy of within 10% or less of the calculated volume.

Although embodiments according to the present invention are described herein with respect to the deposition device 125, any suitable deposition device can be used. In some embodiments, a syringe pump can be used to aspirate a sample solution, and then a digitally controlled gas pressure system can be used to expel a controlled volume of liquid. For example, an isolated solenoid dispensing system, such as is available from Innovadyne Technologies, Inc., Santa Rosa, Calif. (U.S.A.) can be used. Such liquid dispensing solutions typically include a dispensing path that dispenses solution via an orifice, a rapidly actuating solenoid dispensing valve and a controlled pressurized liquid or fluid source. A hybrid valve can connect the dispensing path alternatively to a syringe so that the solution can be drawn into the dispensing path via the orifice when the hybrid valve is connected to the syringe. After filling the dispensing path with solution, the hybrid valve connects the dispensing path to the controlled pressurized liquid source. The pressurized liquid source enters the dispensing path, and a corresponding volume of the solution is displaced so that it exits the dispensing orifice. The amount of the pressurized liquid source entering the dispensing path can be controlled by a micro-solenoid valve and a digital pressure regulator. As the fluid leaves a dispensing orifice of the dispensing device, the velocity and energy of the fluid displacement as the fluid is displaced from the device enables the surface tension of the dispensed liquid to separate the dispensed liquid from the device. Accordingly, such devices can be referred to as "non-contact" devices because contact with the dispensing surface is not required to separate the liquid droplets from the device. Exemplary deposition devices and deposition techniques for depositing controlled volume droplets are described, for example, in U.S. Patent Publication Nos. 20070155019, 20030170903, 20030167822 and 20030072679 and in U.S. Pat. Nos. 7,135,146; 6,983,636 and 6,852,291; the disclosures of which are hereby incorporated by reference in their entireties.

Figure 4B:
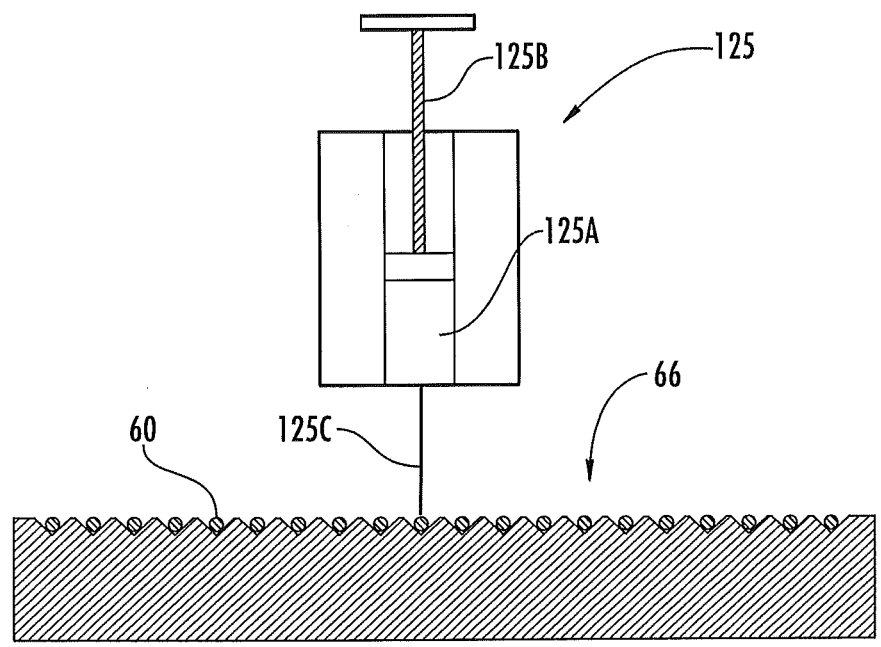
FIG. 4B is a schematic diagram illustrating a micro-syringe deposition system for use with a cartridge of substrates according to some embodiments of the present invention.
Figure 4C:
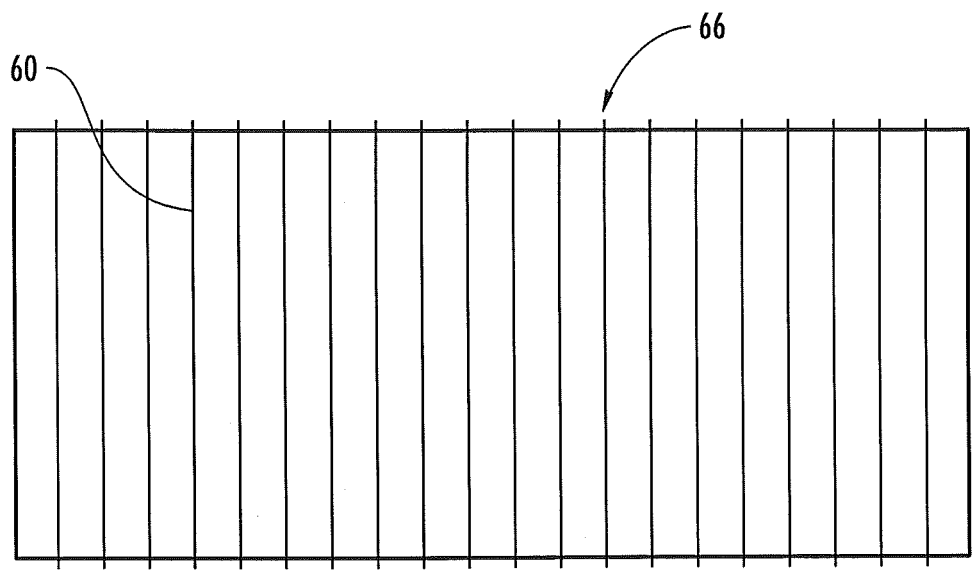
FIG. 4C is a top plan view of the substrate cassette of FIG. 4B.

In some embodiments, commercially available devices, such as the isolated solenoid dispensing systems described above, can be configured to accept microtiter plates; such devices can be adapted to deposit a solution including the radioactive material on a substrate or a plurality of substrates positioned on a cassette as described with respect to FIGS. 4B-4C. When the deposition process is completed, the remaining radioactive solution can be expelled into a recycling container and the syringe tip can be cleaned in water to reduce the formation of salt crystals in or on the syringe tip to reduce or eliminate clogging.

The volume of the solution can be about 75 nanoliters; however, the concentration of radioactive material/drop volume can be selected (e.g., 50-100 nanoliters) to provide a desired radioactivity (higher or lower around the central value). In some embodiments, the radioactive material is in a salt solution, such as $Pd(NH_3)_4Cl_2$. One technique for controlling the concentration of the radioactive material in a volume of solution is to evaporate a solution leaving the salt residue, which is then weighed before being reconstituted into a solution using an appropriate volume of solvent (e.g., water and ammonium hydroxide) to provide the desired radioactivity per volume. The ammonium hydroxide can be present at 10% or greater (e.g., 28-30%) for a radioactive salt to dissolve. The solution can be concentrated to correspond to a range of clinically desired levels of radioactivity, and the volume of the solution drop can also be modified to enhance or reduce the activity in a given globule or well.

The radioactive material can be formed using a radioactive precursor material so that it is radioactive at the time that it is deposited on the device 60 or, in some embodiments, the radioactive material can be in an inactive form during deposition and can be irradiated (e.g., by neutron bombardment) after it is deposited and/or cured to provide a radioactive device.

Figure 4D:
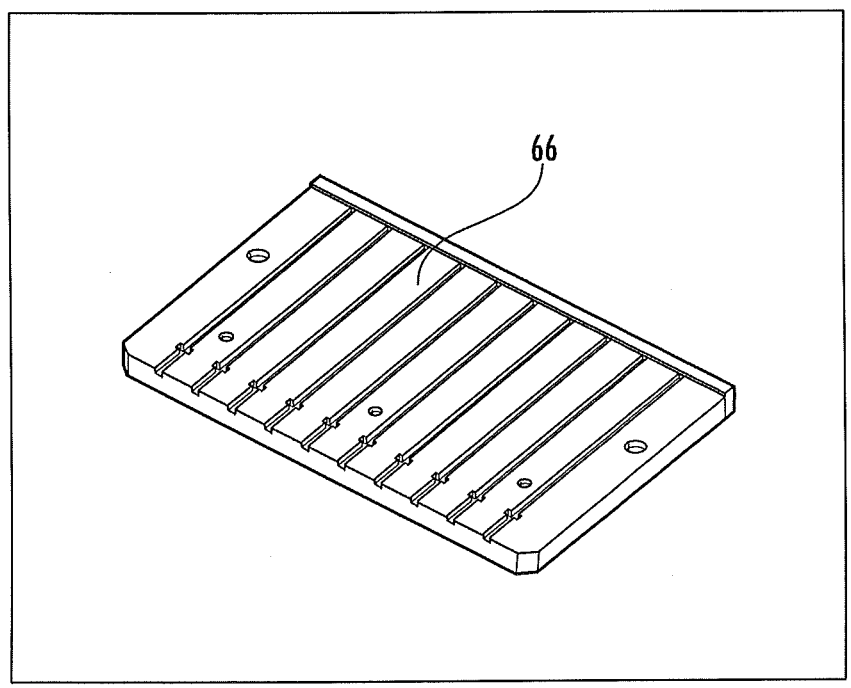
FIG. 4D is a perspective view of a cassette according to some embodiments of the present invention.

In some embodiments, as shown in FIG. 4B-4C a plurality of substrates 60 can be positioned on a cassette 66. The cassette 66 includes grooves, and the substrates 60 are positioned in the grooves. The deposition device 125 of FIG. 4A can be used to deposit radioactive material or other materials such as a precipitation solution on the substrates 60. For example, as shown in FIG. 4B, the deposition device 125 is a micropipette having a reservoir 125A, a plunger 125B and a micropipette needle 125C. The plunger 125B pushes a desired amount of material through the needle 125C and deposits globules of the material at desired positions on the substrates 60. FIG. 4D is a schematic drawings of a cassette 66 for depositing radioactive material on the substrates. In some embodiments, the substrates 60 can be positioned on the substrate cassette 66, and a biocompatible coating or tube can be positioned in grooves on the cassette 66 or on another cassette so as to be aligned with the substrates such that the substrates can be pushed or urged into a biocompatible tube.

Figure 5A:
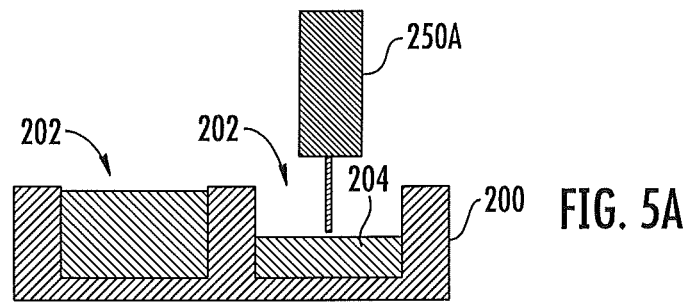
FIGS. 5A-5D are schematic diagram illustrating systems and methods for chemically precipitating a water insoluble radioactive material from a solution according to some embodiments of the present invention.
Figure 5B:
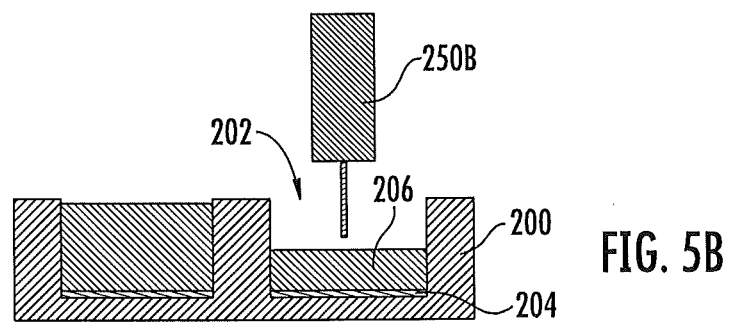

Exemplary techniques for chemical precipitation to provide a water insoluble radioactive material will now be described. As shown in FIG. 5A, a substrate 200 includes a plurality of microwells 202. A deposition device 250A, such as a micropipette or micro syringe, deposits a radioactive material 204 in the form of a solution in the microwell 202. For example, the solution can be tetraamine palladium chloride in ammonium hydroxide or palladium chloride in hydrochloric acid. The volume of the solution of radioactive material 204 can be calculated to match the desired amount of radioactivity in the well. In FIG. 5B, a chemical precipitation solution 206 is deposited in the well on the radioactive material 204 by a deposition device 250B, such as an ink jet deposition device. For example, the precipitation solution 206 can be a mixture of sodium borohydride and sodium hydroxide in sufficient amounts for a reaction to occur to precipitate out the palladium metal, which is then insoluble. The solution 206 and any remaining amounts of the solution containing the radioactive material 204 can be allowed to dry.

Figure 5C:
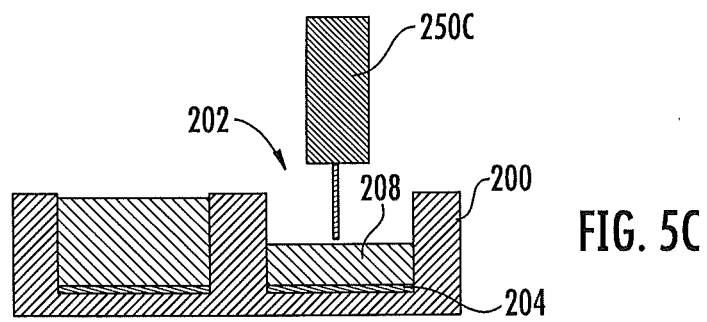
Figure 5D:
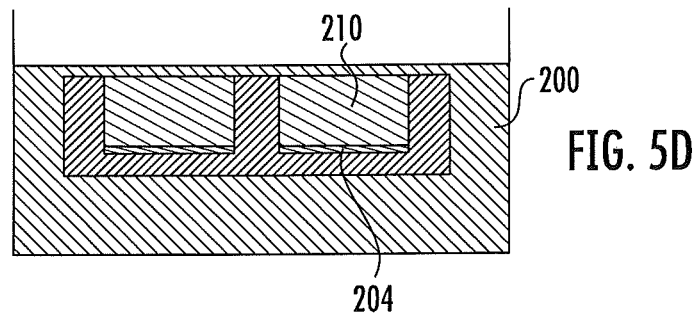
Figure 5E:
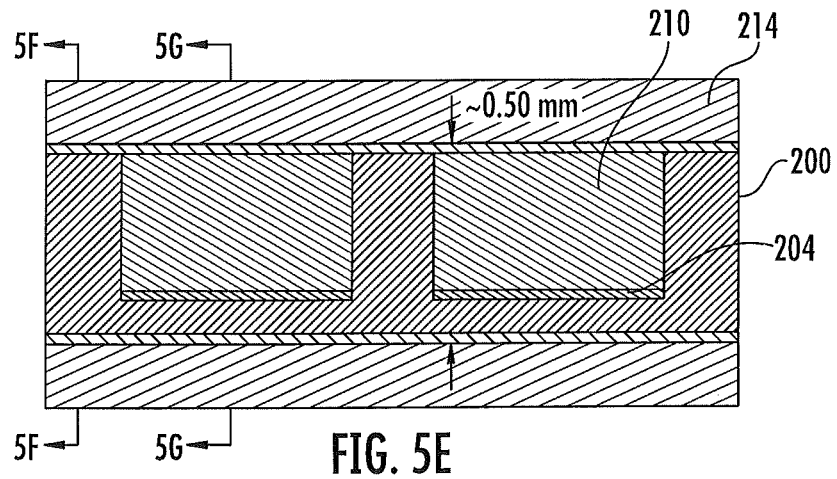
FIG. 5E is a schematic diagram of a brachytherapy device formed from the systems and methods of FIGS. 5A-5D.
Figure 5F:
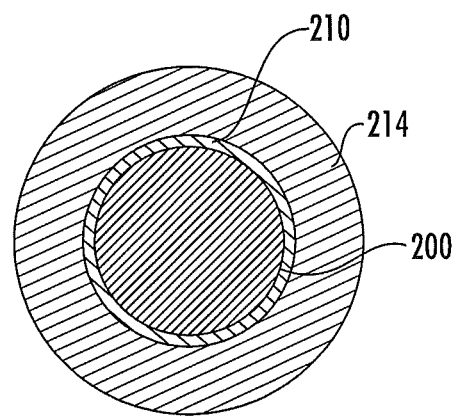
FIG. 5F is a cross sectional view taken along lines 5F-5F in FIG. 5E.
Figure 5G:
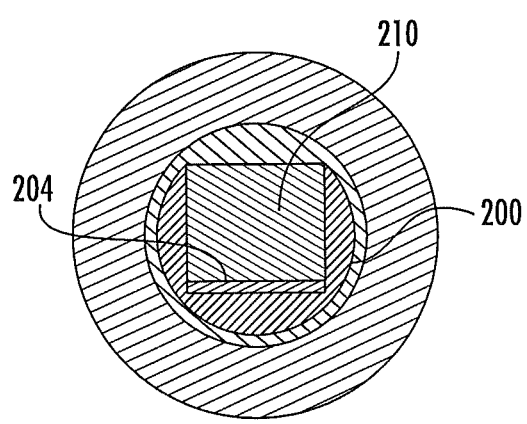
FIG. 5G is a cross sectional view taken along lines 5G-5G in FIG. 5E.

In FIG. 5C, the wells 202 are filled with a sealant 208, such as medical grade epoxy. The sealant 208 can then be cured, for example, by thermal or UV curing based on the type of sealant used. As shown in FIG. 5D, the substrate 200 can then be cleaned with a cleaning solution 212 using known techniques to remove any exposed radioactive material. The radioactive material 204 is in a water insoluble state and sealed by the sealant 208 to reduce or prevent leakage into the body. As shown in FIGS. 5E-5G, the substrate 200 can also be inserted into a sheath 214 to further reduce the risk of radiation leakage.

Figure 6B:
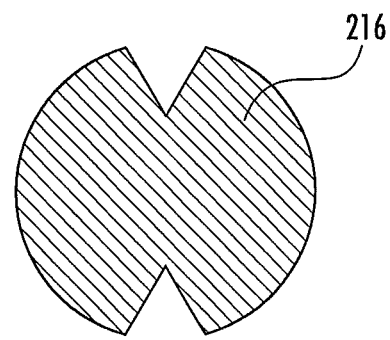
FIG. 6B is a cross sectional view of the radiographic marker of FIG. 6A.
Figure 6C:
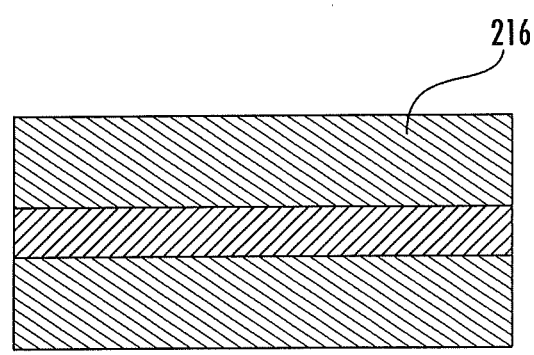
FIG. 6C is a schematic view of the radiographic marker of FIG. 6A.

As shown in FIG. 6A-6C, a radiographic marker 216, such as a gold wire, can be affixed to the ends of the substrate 200 so that the device can be more readily imaged. The radiographic marker 216 can include notches 216A for allowing sealant 208 to be injected into the sheath 214 by a sealant injector 260. As shown in FIGS. 7A-7B, the ends of the resulting device can be trimmed (FIG. 7B) and a plug 218, such as a polymeric plug, can be inserted on the ends of the device for further sealing and containment of the radioactive material 204. In some embodiments, radiographic markers can be placed directly in the wells 202.

According to some embodiments of the present invention, a radioactive material in a solution can be converted to a water-insoluble form by thermal decomposition. In particular embodiments, a silicon substrate or other suitable material that can withstand the thermal processing steps can be used. For example, as shown in FIGS. 8A-8C, a carrier 300, such as a glass or ceramic carrier, includes a plurality of holders 302 for holding a plurality of substrates 310. As shown in FIG. 8C, vacuum holes 300H can be drilled in the carrier 300 to enable immobilization of the substrates 310.

In particular embodiments, the substrates 310 are silicon. The density of silicon is ~2.3 g/cc and thus is denser than polymers (which are all roughly 1 g/cc). For a 20 KeV photon (slightly less than the primary Pd-103 photons), the mass attenuation coefficient is roughly 5.3, and the mass attenuation coefficient for water is 0.81. Accordingly, a 100 µm (about 4 mils) thick layer of silicon can lead to a 5% attenuation of the photons (whereas a 300 µm layer of polymer would be about 2.5% attenuation). Small silicon chips can be even thinner than 4 mils.

In some embodiments, the solution can be converted to a water-insoluble form at relatively low temperatures. For example, when $Pd(NH_3)_4Cl_2$ solution dries thoroughly it forms $Pd(NH_3)_2Cl_2$, which can be thermally decomposed at about 290° C. leaving palladium metal. This processing temperature is consistent with certain polymers, such as silicone, and thus presents a format whereby a polymer can be used as the substrate for the conversion of Pd salt into water insoluble Pd metal.

As shown in FIGS. 8D-8F, a deposition device 350, such as a microsyringe or micropipette, can be used to deposit a radioactive material 304 in the form of a water soluble solution on the substrates 310 (FIGS. 8D-8F). Silicon is hydrophobic, and therefore, the solution may bead up. In some embodiments, the silicon surface is substantially free of other layers or materials. However, surface treatments and/or other material/layers can be used. In some embodiments, a silicon dioxide layer is on the silicon surface in a pattern. The silicon dioxide layer is hydrophillic, and therefore can provide a surface or platform for the radioactive material solution. The volume of the solution can be about 50 nanoliters or about 0.46 mm in diameter; however, the concentration of radioactive material/drop volume can be selected (e.g., 75 nanoliters, or 50-100 nanoliters) to provide a desired radioactive activity. In some embodiments, the volume of the material 304 deposited on the substrates 310 can vary, e.g., to create a variable and/or customized radiation pattern. The radioactive material 304 is then dried (FIG. 8F). For example, the radioactive material can be a palladium compound, such as tetraaminopalladium chloride. However, the resulting dried radioactive material 304 in FIG. 8F is in a water soluble form.

As shown in FIG. 8G, the radioactive material 304 on the carrier 300/substrate 310 is thermally decomposed at a sufficient temperature (e.g., above about 650° C., e.g., for palladium chloride to form a water insoluble precipitate of the radioactive material. In some embodiments in which the substrates 310 are silicon substrates, a silicon compound, such as palladium silicide, can be formed when the radioactive material 304 is heated on the substrate 310. As shown in FIG. 8H-8I, a protective coating 306, such as epoxy, can then be applied to the substrate 310. A placement device 360, such as a "pick-and-place" machine, can move the substrates 310 with the water insoluble radioactive material 340 thereon to an adhesive 322 (such as epoxy) on a polymer carrier core 320. The core 320 can be formed of a suitable material that can be more flexible than the substrates 310. As shown in FIGS. 8J-8N, the polymer core 320 can be inserted into a sheath 330 (FIG. 8J), filled with a sealant 322 by a sealant injector 370 (FIG. 8K), cured and/or trimmed (FIG. 8L). Moreover, radiographic markers 380 can also be added to the polymer core 320 (FIG. 8M), e.g., for enhanced imaging visibility. For example, a radio-opaque metal, such as gold, can be used as a marker 380 for increased x-ray visibility. In some embodiments, the polymer core 320 can be cut or sized to a desired length for implantation (FIG. 8N). In particular embodiments, the core 320, sealant 322, and/or sheath 330 can be formed of a biodegradable polymer so that over time, the core 320, sealant 322, and/or sheath 330 degrades leaving the substrates 310 and radioactive material 304 implanted in the body.

Figure 9B:
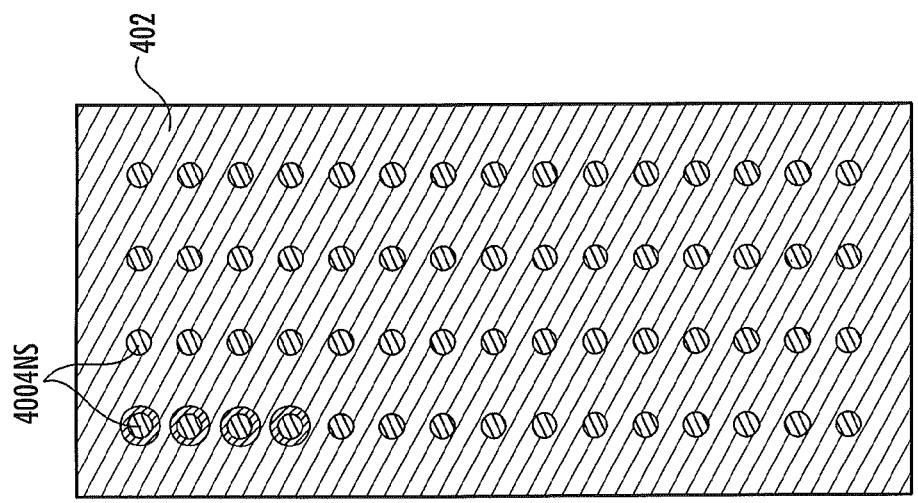
Figure 9A:
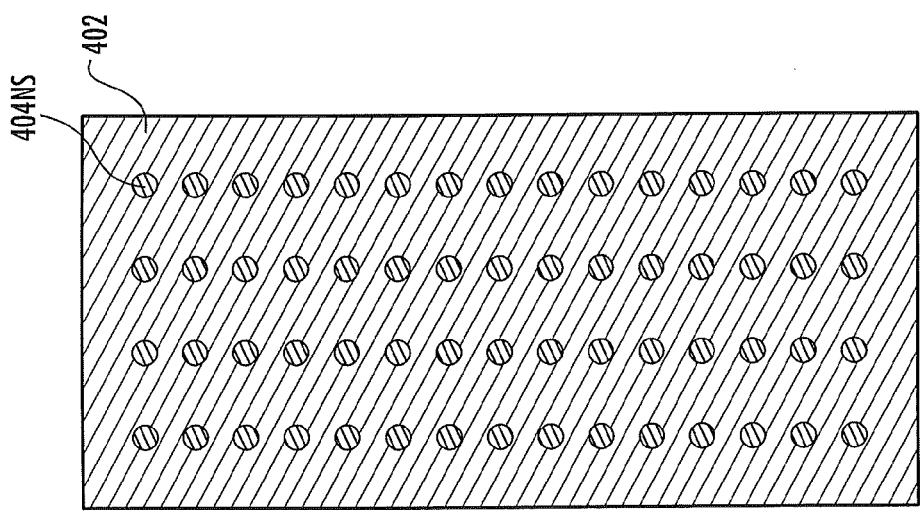

Additional embodiments according to the present invention are shown in FIGS. 9A-9G. As shown in FIG. 9A, a polymer substrate 402 is for the deposition of a plurality of spaced-apart, water-soluble solution droplets of radioactive material 404S. The material 404S can be deposited using various techniques described herein, such as using a syringe or micropipette. In some embodiments, the water-soluble radioactive material can be a salt of Pd-103, such as tetraaminopalladium chloride or palladium chloride. For example, the polymer substrate 402 can be 2 mil nylon 6,6 that is optionally coated with a thin layer of hydrophobic material, such as Epotek 302-3M (which may be thinned and spun onto the polymer substrate 402). Alternatively, the sheet could be PTFE, which is hydrophobic and gives rise to smaller dried residues.

The water-soluble solution of radioactive material 404S is then decomposed to form a non-soluble form of the radioactive material 404NS as shown in FIG. 9B. For example, if a palladium salt is used as the material 404S, the polymer substrate 402 can be exposed to hydrogen or oxygen plasma to decompose the salt into palladium metal.

Although embodiments according to the invention are described above with respect to a plasma decomposition of palladium salt into non-soluble palladium metal, it should be understood that other suitable techniques and/or radioactive materials can be used. For example, in some embodiments, a precipitation solution can be deposited on the material 402S in FIG. 9A so that the water-soluble material 402S chemically precipitates to a water-insoluble form to provide the material 404NS of FIG. 9B.

Figure 9D:
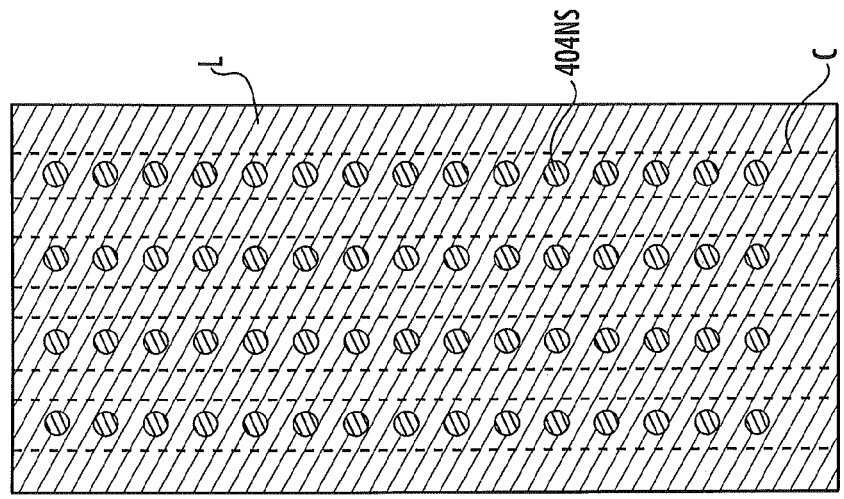
Figure 9C:
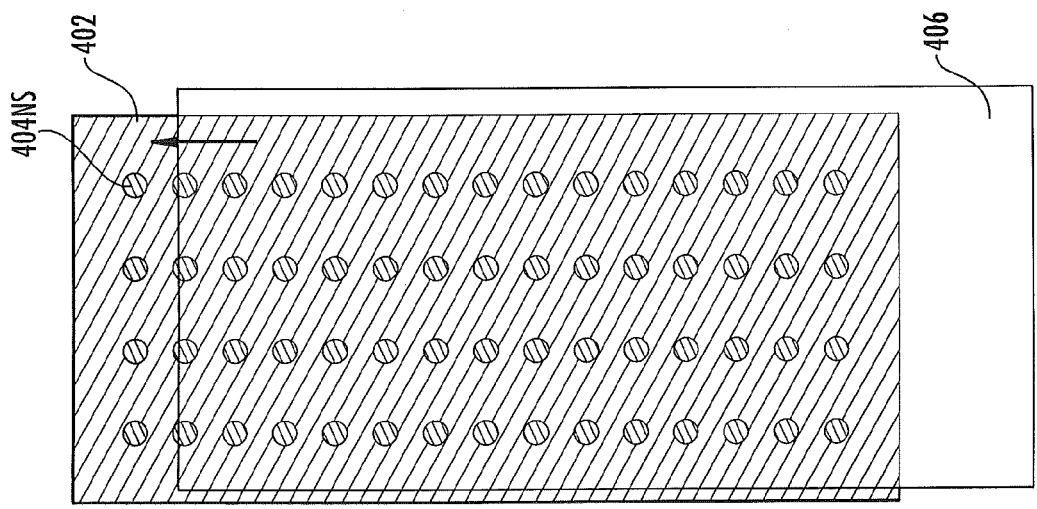

As shown in FIG. 9C, a polymer sheet 406 can be adhered or laminated to the substrate 402 to form a laminated structure L as shown in FIG. 9D. As further shown in FIG. 9D, the laminated structure L can be singulated or cut or sized, for example, with a laser cutter, along cut lines C. As shown in FIG. 9E, the resulting laminated core 410, which includes the spaced-apart regions of the water-insoluble material 404NS.

The laminated core 410 can be further coated or enclosed so that the water-insoluble material 404NS is sealed so as to substantially prevent leakage of the insoluble, radioactive material. For example, the laminated core 410 can include a region without the material 404NS for attaching to a thread, such as a nylon thread 412. As shown in FIG. 9E, the thread 412 is used to position the core 410 into a tube, such as a PTFE mold tube 414 with a carbothane sleeve 416. As shown in FIG. 9F, the tube 414 is then filled with epoxy 418. The epoxy 418 is cured, and the sleeve 416 and the epoxy 418 are removed from the sleeve 416 to form a sealed device as shown in FIG. 9G.

Although FIGS. 9A-9G are described above with respect to a polymer sheet 406 that is cut, it should be understood that any suitable configuration can be used.

Although embodiments according to the present invention have been described herein as a string or elongated member (e.g., the polymer core 320) that is implantable in the body, it should be understood that other implantable devices can be formed using the techniques described herein. For example, the substrates 310 can be inserted into a conventional metallic brachytherapy seed structure or in a polymeric brachytherapy seed.

In some embodiments, implantable devices can be provided that are sized and configured to provide brachytherapy to a particular organ or region of the body. For example, radioactive material can be implanted on a polymeric sheet and implanted in the patient. As illustrated in FIGS. 10-11, a generally planar, 2D radioactive sheet 600 is shown. The sheet 600 includes a substrate 602 (which can be formed using a biodegradable or bioabsorbable material), a radiation shielding layer or gold layer 604 on the substrate 602, and a radioactive material 606 on the gold layer 602. As shown in FIG. 12, the sheet 600 can optionally include perforations 608 and/or cut marks 610. The perforations 608 can reduce the amount of substrate material implanted in the body and/or increase fluid exchange between the two sides of the substrate 602, and the cut marks 610 can be used to allow a medical professional to cut and customize a sheet for implantation in the body.

Although described with respect to the sheet 600 in FIGS. 10-11, it should be understood that other configurations can be used. For example, the gold layer 604 is shown as a continuous strip; however segmented gold areas under the radioactive material 606 can also be used. Other radioactive shielding materials can be used for the gold layer 604. In some embodiments, the gold layer 604 is omitted; however, the gold layer 604 can provide radioactive shielding such that the radiation is reduced on one side of the substrate to provide substantially emissions in one direction. Reducing the radiation emitted on the side of the device adjacent the gold layer 604 and opposite the radioactive material 606 can reduce damage to health tissue in certain applications, such as lung cancer, so that the radioactive side of the sheet 600 is implanted adjacent a cancerous site.

In some embodiments, the substrate 602 can be imprinted with a well pattern and the gold layer 604 and radioactive material 606 can be deposited therein. The density and/or size of the radioactive material 606 deposited on the sheet 600 can be controlled as described herein to provide a desired radioactive profile for the sheet 600. In some embodiments, a top sheet of bioabsorbable material can be laminated with bioabsorbable adhesive or otherwise affixed over the radioactive material 606 to provide a generally sealed source. In addition, the substrate 602 can include regions that are substantially free of the radioactive material 606 to provide, for example, a border for surgical attachment. Radiomarkers such as gold squares can be added at various places on the substrate 602 to facilitate radiographic imaging and/or for dosimetry assessment after the implantation is completed.

The gold layer 604 can be deposited on the substrate 602 by shadow masking or using appliqués. The perforations 608 can be formed before or after the deposition of the gold layer and/or radioactive material 606.

The radioactive material 606 can be deposited using the techniques described herein. For example, a palladium (Pd) salt solution can be deposited, such as with a precision deposition system (e.g., an isolated solenoid dispensing system, such as is available from Innovadyne Technologies, Inc., Santa Rosa, Calif. (U.S.A.)). The solution can be dried and/or decomposed into a water-insoluble form using the chemical, plasma and/or thermal decomposition techniques described herein. In some embodiments, the gold layer 604 can be coated with an additional thin polymer layer to provide a pre-treatable surface prior to Pd solution deposition.

In addition, the order of the radioactive layer 606 and the gold layer 604 can be reversed and/or additional substrates or coating layers may be used. For example, as illustrated in FIG. 12A, the radioactive material 606 can be deposited on a substrate 602A as described herein. As shown in FIG. 12B, a gold layer 604 can be deposited on another substrate 602B. The two substrates 602A, 602B may be laminated together to provide substantially uni-directional radiation emissions as shown in FIG. 12C such that radiation is reduced on the side of the device adjacent the substrate 602A.

Embodiments according to the present invention will now be described with respect to exemplary lung cancer brachytherapy treatment.

Lung Cancer Treatment:

Background:

Lobectomy is the standard of care for patients diagnosed with early stage non-small cell lung cancer (NSCLC). However, patients affected by this disease frequently have compromised pulmonary function, which can be clearly documented with pre-operative pulmonary function studies. See M. A. Beckles, S. G. Spiro, G. L. Colice, and R. M. Rudd, "The physiologic evaluation of patients with lung cancer being considered for resectional surgery," *Chest*, vol. 123, pp. 105S-114S, January 2003; J. A. Bogart, E. Scalzetti, and E. Dexter, "Early stage medically inoperable non-small cell lung cancer," *Curr Treat Options Oncol*, vol. 4, pp. 81-8, February 2003; and C. T. Bolliger, "Evaluation of operability before lung resection," *Curr Opin Pulm Med*, vol. 9, pp. 321-6, July 2003. As such, these patients can be predicted to be unsuitable for standard lobectomy. Multiple studies, including a prospective randomized clinical trial from the Lung Cancer Study Group (LCSG) (R. J. Ginsberg and L. V. Rubinstein, "Randomized trial of lobectomy versus limited resection for T1 N0 non-small cell lung cancer. Lung Cancer Study Group," *Ann Thorac Surg*, vol. 60, pp. 615-22; discussion 622-3, September 1995.), have demonstrated the inferiority of sublobar resection alone, showing local failure rates as high as 22%. See T. A. d'Amato, M. Galloway, G. Szydlowski, A. Chen, and R. J. Landreneau, "Intraoperative brachytherapy following thoracoscopic wedge resection of stage I lung cancer," *Chest, vol.* 114, pp. 1112-5, October 1998.; R. J. Landreneau, D. J. Sugarbaker, M. J. Mack, S. R. Hazelrigg, J. D. Luketich, L. Fetterman, M. J. Liptay, S. Bartley, T. M. Boley, R. J. Keenan, P. F. Ferson, R. J. Weyant, and K. S. Naunheim, "Wedge resection versus lobectomy for stage I (T1 N0 M0) non-small-cell lung cancer," *J Thorac Cardiovasc Surg*, vol. 113, pp. 691-8; discussion 698-700, April 1997; R. Santos, A. Colonias, D. Parda, M. Trombetta, R. H. Maley, R. Macherey, S. Bartley, T. Santucci, R. J. Keenan, and R. J. Landreneau, "Comparison between sublobar resection and 125Iodine brachytherapy after sublobar resection in high-risk patients with Stage I non-small-cell lung cancer," *Surgery*, vol. 134, pp. 691-7; discussion 697, October 2003. Additionally, the LCSG demonstrated superior pulmonary function at 12 and 18 months post sublobar resection and brachytherapy compared to the control group treated by lobectomy alone. See R. Santos, A. Colonias, D. Parda, M. Trombetta, R. H. Maley, R. Macherey, S. Bartley, T. Santucci, R. J. Keenan, and R. J. Landreneau, "Comparison between sublobar resection and 125Iodine brachytherapy after sublobar resection in high-risk patients with Stage I non-small-cell lung cancer," *Surgery*, vol. 134, pp. 691-7; discussion 697, October 2003. Some investigators have reported on the multi-week fractionated delivery of post-operative external irradiation following sublobar resection. The addition of external beam radiotherapy has the increased risk of pulmonary fibrosis and radiation pneumonitis as well as a decreased incidence of local control. Patient compliance and completion of total prescribed therapy are frequent problems with high dose external beam radiotherapy. Second line primary therapy in this patient cohort is external irradiation alone, which has been shown to be inferior in terms of local control and overall survival by 15-20% or more. Therefore, patients treated with a non-surgical option have outcomes significantly inferior to surgically managed patients.

Sublobar resection complimented by the intraoperative placement of a Vicryl® mesh substrate impregnated with $^{125}$I ribbons affixed in a parallel planar array designed to deliver a dose of between 100 and 120 Gy to 0.5 cm from the perpendicular plane of the implant has been investigated. See R. Santos, A. Colonias, D. Parda, M. Trombetta, R. H. Maley, R. Macherey, S. Bartley, T. Santucci, R. J. Keenan, and R. J. Landreneau, "Comparison between sublobar resection and 125Iodine brachytherapy after sublobar resection in high-risk patients with Stage I non-small-cell lung cancer," *Surgery*, vol. 134, pp. 691-7; discussion 697, October 2003; and T. A. d'Amato, M. Galloway, G. Szydlowski, A. Chen, and R. J. Landreneau, "Intraoperative brachytherapy following thoracoscopic wedge resection of stage I lung cancer," *Chest*, vol. 114, pp, 1112-5, October 1998. Since implementation, more than 400 patients have been treated with this technique. The local failure rates have been shown to be approximately 1-3% in properly selected patients. The radiation is delivered in a very uniform manner with 100% patient compliance. Additionally, the delivery of radiotherapy is immediate and constant over the permanent time frame of the implant. This precludes the approximately 6-week course of external radiotherapy, decreasing time of treatment, inconvenience to the patient and overall cost. The morbidity associated with this procedure is low with no increase in infection or morbidity in patients treated with brachytherapy versus those treated with sublobar resection alone. One incidence of fatal vacular rupture developed in a patient whose dose was supplemented with external irradiation (8). However, this is now relatively contraindicated and the brachytherapy procedure is currently not performed in patients who require post-operative external irradiation. These include patients with positive mediastinal nodes proven by frozen section at the time of surgery. The American College of Surgeons Oncology Group (ACOSOG) has instituted protocol Z4032 "A randomized phase III study of sublobar resection versus sublobar resection plus brachytherapy in high risk patients with non-small cell lung cancer (NSCLC), 3 cm or smaller". "ACOSOG protocol Z4032."

One of the potential problems with brachytherapy in this circumstance is a lack of a reliable and consistent delivery substrate which can be custom fitted to the individual patient. $^{125}$I ribbons come pre-formed with 1.0 cm spacing between the seeds and 10 seeds per ribbon. This yields an effective treatment length of 9 cm. Many times this length is unnecessary and a shorter length would be preferred. In addition, there is generally a 1.0-1.5 cm spacing between each of the parallel ribbons of the $^{125}$I implant and a substrate with a more conforming size would be preferred; if one existed. Although the technique has worked well in many patients, a significant number of implants are aborted intraoperatively as the constructed mesh would be in contact with major vascular structures (excluding the aorta) or major bronchial structures. A substrate which could be custom tailored and fitted intraoperatively would provide a marked improvement in the safe and limited delivery of radiation. Additionally, one in which the radiation could be effectively delivered in one direction could significantly limit the potential for unnecessary exposure to normal organs or tissues at risk. These approaches would potentially increase the numbers of patients amenable to the limited surgical approach and potentially decrease the risks associated with the procedure from an implant that was larger than necessary.

Precision deposition of radioisotope in solution can be performed as described herein on a substrate sheet that is sized and configured for implantation adjacent a patient's lung. The soluble isotope is converted into an insoluble form as described herein. Several water soluble precursor formats could be used, including tetraaminepalladium chloride: $Pd(NH_3)_4Cl_2$. This material can be obtained commercial with a nominal specific activity and activity per unit volume of solution. The material is first evaporated, leaving behind the palladium salt, and then reconstituted to a concentration that yields the targeted activity per unit volume needed for the desired air kerma strength of the finished device. That is, the desired precision in apparent activity is achieved by controlling the volume and activity per unit volume of a molecularly dispersed compound of the Pd-103 isotope.

There are several commercial dispensing systems capable of producing drops sizes in the 100 nl range. This process uses a microsyringe pump assembled with an x-y-z stage to allow for precision placement of drops onto a substrate.

Once dried, the 4-ammonia Pd salt loses two ammonia molecules to become $Pd(NH_3)_2Cl_2$. This compound will decompose, thermally, at about 290° C. See L. A. Solov'yov, A. I. Blokhin, M. L. Blokhina, I. S. Yakimov, and S. D. Kirik, "Powder diffraction study of the crystal structure of trans-Pd (NH3)2C12," *Journal of Structural Chemistry*, vol. 38, 1997. Although certain polymers, like silicone, will withstand this temperature, some will not and this can be limiting in terms of a choice of materials. The 2-ammonia salt can also be decomposed in an oxygen plasma and this is the technique can also be used to create the subject devices. A planar-type reactor is used with a power level of ~200 watts. The oxygen pressure in the chamber is typically 100 mTorr. The yellowish salt of palladium visually turns black (non-water soluble Pd metal) in the plasma. As noted below, assays of the material after treatment confirm that the salt has been decomposed (chlorine and ammonia go off as gases) and only metallic Pd remains. It is also possible to use an optical spectrometer to record the evolution of the gas species, thus creating an endpoint detection mechanism for process monitoring.

Once cured, the devices can then be trimmed to final length and are then ready for dosimetric evaluation and sterilization (e.g., in ethylene oxide (ETO)). It should also be noted that gold radiographic markers can be inserted into one or more of the nylon wells to enable visualization in clinical x-ray imaging runs (gold is not placed in wells that contain pd metal). Because of the extended length of this source, a well chamber with a long "sweet spot", the IVB-1000, is used so that the air kerma strength of the entire source can be acquired. Additionally, the source can be moved along a cylindrical aperture in the chamber to assure that the activity per unit length is within tolerance. Note that it is possible with this method to vary the activity per unit length, which opens the possibility of a truly customized source. The IVB-1000 well chamber will be maintained in calibration with reference to a VAFAC (12) device. Monte Carlo simulations of this source can also be performed.

To check for sealed-source integrity, a source is soaked in water (ISO 9978:1992(E)) for 4 hours at 50° C. and then the soak solution is assayed. In the test results summarized below, a scintillation fluid is added to the soak solution and then it is placed in an integrating sphere for event counting. The ISO metric is activity less than 5 nCi after this assay. Devices were evaluated according to the ANSI N43.6-2007 standards to ensure that physical damage caused by various factors would not result source leakage (specifically, the device is designated ANSI 07C22XX1X (X)).

Results:

Biocompatibility Testing:

Toxikon (Bedford, Mass.) evaluated non-radioactive analogs of finished devices. Obviously, radioactive devices would create significant tissue damage, thus masking any effects of the materials (though the devices were "aged" by administering 7 kGy of gamma radiation prior to animal testing). Tests were completed for: cytotoxicity, sensitization, irritation, and systemic toxicity and all results were negative for induced changes relative to controls. Long-term (subcutaneous) implantation tests were performed for 2, 4, 13, and 26 weeks with histopathology being performed after explantation. There were no changes recorded relative to controls. Also, an in-house image study of the explanted devices showed no apparent degradation of the polyurethane or epoxy materials. Therefore, it was concluded that the materials are safe for permanent implantation in the current device configuration.

Materials Analysis: Development of the oxygen plasma process progressed through the use of a non-radioactive mimic of the Pd salt solution. This allowed for the use of standard assay tools to hone the process parameters. In particular, an x-ray emission analyzer (EDS) was used to obtain elemental concentrations of the processed salt. As shown below, well processed samples only had Pd remaining whereas incompletely processed material gave a measurable chlorine peak (the assay was not really sensitive to ammonia, nitrogen). This tool was used to establish proper drying and process time values so that consistent conversion of the salt to metal was obtained. It should be noted that the effective density of the converted Pd metal residue is significantly lower than solid, sintered metal. This is because the dried crystals, initially, have significant amounts of trapped water and further the crystals are highly dendritic. When the salt is decomposed, the Pd grains appear to be sub-micron in size and are loosely held in a spongy matrix. In-house testing showed that there is minimal self-attenuation of the "sponge," thus simplifying the task of achieving the target activity.

Monte Carlo Simulation: The device geometry was evaluated using the MCNP5 code. As noted above, the effective density of the unconsolidated Pd metal residue is much lower than that of the pure metal. The simulation assumed a thin layer of metal in the well with an effective density of a few percent of dense metal value. This simulation will be re-run with different dispersions of the metal to check for consistency. Because of the close placement of the wells, the source will be indistinguishable from a purely linear source. The MC predictions can be evaluated with empirical measurements, e.g., using a VAFAC electrometer.

Sealed Source Testing: The basic sealed-source test conditions were described above. The devices were subjected to ANSI standard testing, as well as certain special tests, as listed below:

A temperature test from −40° C. (20 min) to 80° C. (1 hour). This is to simulate changes in temperature beyond which the finished devices would ever experience.

An external pressure test from 3.6 psi (vacuum) to atmospheric (simulate possible air travel).

A special impact test involving a "heel crush" to simulate the device being stepped on by a user (155 pounds for 10 seconds).

A special puncture test using forceps to simulate excessive gripping of the device by a user (5 pounds of force using serrated metal tweezers).

A special bending test. The device is bent over a cylinder 5D in diameter, where D is the device diameter.

A non-ANSI test under autoclave conditions to assess whether any leakage of the isotope occurs.

A non-ANSI test wherein the device is cut in half (in the middle of a well) to assess the potential for contamination should the device be accidentally cut.

A non-ANSI test in which each of the devices is soaked again for 1 week (at room temperature), after which the soak solution is again assayed for any contamination.

All of the tested samples were checked, as described above, for evidence of leakage. The only sample that showed a reading above background was the one that was purposely cut in half through a well containing Pd metal (roughly 35 nCi of leakage, still quite small). Most probably the soaking action loosened Pd grains that simply fell out into the solution. All of the samples were then soaked for an additional period of 1 week at room temperature in saline and the scintillation study was performed again. As before, only the purposely cut sample showed any signal above background (this time ~10 nCi). Therefore, the data indicate that the sealing method is effective.

Linear Sources:

A linear, polymeric source can provide the following attributes:

Polymer composition reduces intersource attenuation (13)

A linear source can achieve the same DVH as seeds with ~20% less apparent activity (14)

The dose fall-off has a different length dependence RE seeds, which should provide greater immunity to dose distortion, e.g. from edema or needle misplacement (15, 16)

The activity per length can be changed as desired

Placement of markers can be optimized for the application

Precision definition of activity per unit length

Straightforward assembly resulting in "stranded" sources

Physically robust materials

Low cost-of-goods due to simple processing steps and significantly less Pd-103 required.

The flexibility of the production method can be extended to a 2-dimensional source type so as to provide a type-match for post lung resection brachytherapy.

Applicability to 2D Bioabsorbable Source:

The deposition system described herein can be used for a flat, 2-dimensional substrate, and a desired activity per unit area can be established The plasma oxidation method can be used irrespective of the distribution of the Pd salt precursor (as long as the deposit size is not too large, which can extend processing time beyond acceptable limits) and irrespective of the polymer used for the substrate. A 2D radioactive sheet can be formed with sealed source integrity on a bioabsorbable substrate, The deposition pattern and/or shape of the device can be matched to the desired therapy plan values.

Monte Carlo (MC) modeling will be performed using N-Particle 5 (MCNP5) transport code with updated DLC-146 photon cross sections. Where possible, specific atomic compositions of the materials will be used to ensure an accurate end result. The two primary goals under the modeling task are: 1) evaluate the isodose profile of the 2D sheet and 2) provide relative dose estimates (as a function of location) so as to mesh with the empirical measurements to be performed. The linear source aspects already investigated for the 1D source will be taken advantage of in the 2D design. Various Pd metal dot spacings will be evaluated.

In some embodiments, the user can physically trim the 2D source sheet in the operating room as needed based on the patient's specific anatomy after the resection is performed, which can not be feasible with current seed-based arrangements. For this to be achieved safely, cut lines will be indicated on the sheet so as to avoid slicing through the Pd metal regions themselves. The effect of such cuts will be evaluated using MC modeling as well.

About fifteen to twenty microns of gold will attenuate the primary Pd-103 x-rays by 90% or more. Therefore, a design that incorporates gold discs of this thickness under the sites where Pd metal is placed will create a significant anisotropy in the dose on one side of the 2D sheet versus the other. The appeal of this approach is to mitigate dose delivered to collateral tissue while maintaining adequate, dose to the surgical site. Using standard photolithographic patterning, patterning gold in the necessary array of dots is readily achievable. Gold is well known to be biocompatible and the thickness needed will not be visible on diagnostic x-rays. The exact size of the gold dot relative to the Pd metal dot needed to achieve this effect will be established with MC modeling.

Sample devices can be made and empirical dose measurements can be conducted, for example, using non-absorbable substrates (e.g., nylon 6,6) to construct sample devices for evaluation with a lung phantom. Empirical dose measurements can be made at selected points in the phantom to provide quantitative validation of the Monte Carlo model predictions.

Fabrication: For efficiency, 2D sources will be made with a nylon substrate for dosimetric tests while candidate bioabsorbable materials are evaluated in parallel. The techniques described herein to produce the linear sources will be applied to a 2D substrate. Specifically, the substrate will be affixed to a plastic cassette and a pattern of Pd salt dots will be applied using the microsyringe deposition system. After drying, the salt will be decomposed in oxygen plasma in situ. (For the anisotropic test device, gold dots will be pre-patterned on the substrate prior to the application of Pd material.) Previously, the endpoint (full conversion to Pd metal) was determined empirically by running the plasma process at varying times and using EDS analysis to search for salt remnants (specifically a chlorine peak). An optical emission spectroscopy system can be used for endpoint detection. This system, produced by Ocean Optics (Dunedin, Fla.), will enable the process to be monitored over time and stopped when the decomposition products are exhausted. For the purposes of these tests, the Pd metal regions will be covered with a thin layer of medical grade epoxy to seal them. This is effectively how the 1D devices were sealed and validated. These materials will be input into the MC model to ensure a proper match to the empirically derived dose readings. Additionally, gold squares of sufficient thickness to be seen with diagnostic CT will be added to the 2D source so as to enable post-implantation identification of the source location for use in clinical dosimetry (generally ~30 days after the surgery).

Dosimetry: In this task the Monte Carlo calculations will be validated in a phantom following the American Association of Physicists in Medicine Task Group Report 43 (AAPM-TG43) dosimetry protocol. Because the depth of interest in the lung brachytherapy procedure is 0.5 cm, we propose to measure the relative longitudinal dose distribution at that distance in water and lung equivalent phantom material. The Pd103 rectangular substrate sheet will be sandwiched between two slabs of 0.5 cm thick material that are equivalent to water in the first case and lung in the second case in terms of dose deposition from keV-range photons. One radiochromic film sheet will then be placed on each side of the setup, to measure the dose distribution on both sides of the Pd103 sheet. An additional 2 cm of water or lung equivalent material will be added on top of each film to account for backscatter dose. The films will then be processed, digitized and analyzed using the RIT software (Radiological Imaging Technology, Colorado Springs, Colo.) to obtain a relative dose distribution.

The radial distribution relative to the depth of 5 mm will be measured in an acrylic slab phantom (PTW type 2962, New York, N.Y.) using a parallel plate chamber (PTW model 23342). The measurements will be made at distances of 1 to 50 mm above the center of the Pd103 sheet, in 2 mm increments. Additionally an absolute dose measurement will be made with the parallel plate chamber at a point 0.5 cm above the center of the Pd103 sheet.

All previously described measurements will be repeated for the anisotropic source sheet, which has a higher emission on one side by attenuating the Pd103 using patterned gold dots on the one side. Measurements will also be performed in a similar manner using the standard I-125 vicryl mesh of the same size as the Pd103 patch to allow comparison of dose distributions.

Several candidate bioabsorbable materials can be evaluated for biological half-life versus sealed-source containment needs. Common bioabsorbable materials Materials: Copolymers and homopolymers of glycolic acid (GA) and L-lactic acid (LA) have generally excellent toxicological histories when used in medical implants. The focus for the current evaluation will be on copolymers using a blend of these two base materials. Vicyrl (Polyglactin 910), for instance, is formed with a 90:10 GA-to-LA blend. Another material described in the literature (17) for orthopedic uses is a mixture of 18:82 GA-to-LA blend to achieve longer-term stability in the body.

|  | poly-GA | poly-LA | 90:10 of PA:LA (vicryl) |
|---|---|---|---|
| Period until polymer mass becomes zero (at 37° C. in saline) | 60-90 days | 3-5 years | 70 days |
| Period until tensile strength of polymer drops by 50% (at 37° C. in saline) | 14-21 days | 6-12 months | 21 days |

Various commercially available materials can be used, In addition to Vicryl, there are many other materials that have been investigated such as: Atrisorb, Resolut, Lactosorb, etc.

Pd-103 has a 17 day half-life and thus at 60 days, the source strength is down over 90%. For I-125, the half-life is 60 days and thus it takes 200 days for the source strength to decay by 90%. Thus, the task of balancing radioactive half-life with bioabsorbability may favor Pd-103. However, 1-125 has thus far been used exclusively for brachytherapy after sub-lobar lung resection. In terms of radiobiological differences between the isotopes, the most extensive comparative data is from use in the prostate gland (18). Despite theoretical arguments (using the linear-quadratic model) that would favor Pd-103 for more rapidly dividing cell types, there is no clear evidence of differences in outcomes. Further, the anisotropic sheet approach can allow for a net reduction of dose rate to surrounding tissues and organs.

Accelerated Life Tests and Sealed-Source Integrity: Accelerated life testing in physiologic saline at temperatures in the 45-50° C. range will be undertaken. Typically this temperature range will provide a 2.5-3.5 times increase in the hydrolytic degradation of bioabsorbable polymers (19). The tests will investigate structural as well as sealed-source integrity. For the former, a non-radioactive analog of the Pd salt precursor will be used so that measurements of dissolution using HPLC (high performance liquid chromatography can be performed without the risk of contaminating equipment. Identically arranged test fixtures will incorporate Pd-103 so that soak samples can be taken and added to a scintillation fluid for counting purposes (to determine the extent of any radiation leakage into the soak solution).

Smooth layers (at least locally under the Pd material) of the substrate material are needed to contain the palladium grains that form after plasma oxidation. Thus a mesh, per se, may not be useful. Though all of the polymers of interest will be etched by the oxygen plasma, the rate of material removal is small (microns). Devices sealed with medical grade epoxy will be used as controls, as those materials will not degrade over the time scale of interest and have been proven to work successfully in our process to maintain sealed-source integrity. The following sequence will be used for each test arm (degradation and sealed-source):
  Soak test structure at elevated temperature in physiologic saline for 3-7 days (based on a determination of degradation acceleration at the test temperature)
  Remove the test structure (unless it is no longer self-supporting) and place it in fresh soak solution
  Assay the old soak solution by HPLC or in a counting rig as appropriate
  Plot these data to obtain a rough kinetics profile of physical and sealed-source degradation with time (referred to 37° C.).

The foregoing is illustrative of the present invention and is not to be construed as limiting thereof. Although a few exemplary embodiments of this invention have been described, those skilled in the art can readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of forming a low-dose (LDR) brachytherapy device, the method comprising:
  forming a plurality of substrates having a water-insoluble form of a radioactive material thereon; and
  positioning the plurality of substrates on a carrier core; and
  forming a medical device from the carrier core and the plurality of substrates, wherein forming the plurality of substrates having the water-insoluble form of the radioactive material thereon comprises:
  depositing a solution comprising a soluble form of a radioactive material on a substrate; and
  converting the soluble form of the radioactive material to a water-insoluble form of the radioactive material on the substrate, and
  wherein converting the soluble form of the radioactive material to a water insoluble form of the radioactive material comprises exposing the substrate and the water-soluble form of the radioactive material to plasma thereby decomposing the soluble form of the radioactive material to a water-insoluble form of the radioactive material.

2. The method of claim 1, wherein the plasma comprises hydrogen plasma and/or an oxygen plasma.

3. The method of claim 2, wherein the hydrogen or oxygen plasma is at atmospheric pressure or in a partial vacuum.

4. The method of claim 2, wherein the soluble form the radioactive material comprises a salt of Pd-103.

5. The method of claim 4, wherein the salt of Pd-103 comprises tetraaminopalladium chloride.

6. The method of claim 1, wherein the substrate comprises a polymer substrate.

7. The method of claim 1, wherein forming a medical device comprises enclosing the substrates, the carrier core and the water-insoluble form of the radioactive material with a biocompatible material.

8. The method of claim 1, wherein depositing a solution comprising a soluble form of a radioactive material on a substrate comprises depositing an array of spaced-apart globules of the soluble form of the radioactive material on the substrate.

9. The method of claim 8, wherein the substrate comprises micro-wells, and the array of spaced-apart globules are deposited in at least some of the micro-wells on the substrate.

10. The method of claim 8, wherein the substrate is substantially planar.

11. The method of claim 8, wherein forming a medical device from the carrier core and the plurality of substrates comprises:
  adhering a polymer sheet on the substrate and the water-insoluble form of the radioactive material; and
  sizing elongated portions of the carrier core to thereby form a brachytherapy strand.

12. The method of claim 11, wherein forming a medical device from the substrate and the water-insoluble form of the radioactive material comprises:
  positioning the brachytherapy strand in a biocompatible tube;
  filling the tube with a curable thermoplastic resin; and
  curing the thermoplastic resin such that the radioactive material is sealed.

13. The method of claim 1, wherein the solution comprises a soluble form of Pd-103 comprising $[Pd(NH_3)_4]Cl_2$ and/or $PdCl_2$.

14. The method of claim 13, wherein the solution comprises $[Pd(NH_3)_4]Cl_2$ dissolved in ammonium hydroxide ($NH_4OH$) and/or $PdCl_2$ dissolved in HCl.

15. The method of claim 1, wherein the radioactive material comprises I-125.

16. The method of claim 1, further comprising coating the plurality of substrates with a biocompatible coating.

17. The method of claim 16, wherein the biocompatible coating comprises a polyurethane sleeve.

18. The method of claim 17, wherein the polyurethane sleeve has a thickness greater than 150 micrometers.

19. The method of claim 1, wherein depositing the solution comprises depositing discrete, spaced-apart globules of the solution using a solenoid dispensing system having a controlled pressurized fluid source, a micro-syringe pump and/or micropipette.

20. The method of claim 19, wherein a volume for each of the globules is between 5 and 500 nanoliters.

21. The method of claim 19, further comprising depositing the respective volumes of the globules to an accuracy of 10% of an intended volume.

22. The method of claim 19, wherein the globules are spaced apart by about 500-1000 μm.

23. The method of claim 1, wherein each of the substrates is an elongated body.

24. The method of claim 1, wherein depositing a solution comprising a soluble form of a radioactive material on a substrate comprises depositing spaced-apart globules of the soluble form of the radioactive material, wherein the globules have a volume of about 30-200 nanoliters.

\* \* \* \* \*

UNITED STATES PATENT AND TRADEMARK OFFICE
CERTIFICATE OF CORRECTION

| | | |
|---|---|---|
| PATENT NO. | : 9,180,310 B2 | Page 1 of 1 |
| APPLICATION NO. | : 13/692197 | |
| DATED | : November 10, 2015 | |
| INVENTOR(S) | : Black et al. | |

It is certified that error appears in the above-identified patent and that said Letters Patent is hereby corrected as shown below:

Specification
Column 10, Line 34: Please correct "1-125" to read -- I-125 --

Signed and Sealed this
Fourteenth Day of June, 2016

Michelle K. Lee
*Director of the United States Patent and Trademark Office*